United States Patent
Center et al.

(10) Patent No.: US 7,019,118 B2
(45) Date of Patent: Mar. 28, 2006

(54) IL-16 ANTAGONISTS

(75) Inventors: David M. Center, Wellesley Hills, MA (US); William W. Cruikshank, Westford, MA (US); Hardy Kornfeld, Wellesley Hills, MA (US)

(73) Assignee: Trustees of Boston University, Boston, MA (US)

( * ) Notice: Subject to any disclaimer, the term of this patent is extended or adjusted under 35 U.S.C. 154(b) by 329 days.

(21) Appl. No.: 09/929,924

(22) Filed: Aug. 15, 2001

(65) Prior Publication Data

US 2002/0147151 A1 Oct. 10, 2002

Related U.S. Application Data

(62) Division of application No. 09/368,632, filed on Aug. 5, 1999.

(51) Int. Cl.
*C07K 16/00* (2006.01)
*C07K 14/00* (2006.01)
*A61K 39/395* (2006.01)

(52) U.S. Cl. ............... 530/387.1; 530/388.1; 530/389.1; 530/324; 530/350; 424/139.1

(58) Field of Classification Search ............ 530/388.1, 530/389.1, 350, 326, 387.1; 424/139.1
See application file for complete search history.

(56) References Cited

U.S. PATENT DOCUMENTS 5,171,838 A * 12/1992 Chiba .................. 530/326
5,846,933 A * 12/1998 Korngold et al. ............ 514/11

FOREIGN PATENT DOCUMENTS

WO    WO 94/28134    12/1994
WO    WO 97/36606    10/1997

OTHER PUBLICATIONS

Harlow. E., et al. Antibodies, 1988, pp. 76 and 555.*
Moreland et al. Arthritis and Rheumatism, vol. 39, No. 9 (supplement), p. S244, 1996.*
Panayi et al. Arthritis and Rheumatism, vol. 39, No. 9 (supplement), p. S244, 1996.*
Choy et al. Arthritis and Rheumatism, vol. 39, No. 9 (supplement), p. S244, 1996.*
Connolly et al. Arthritis and Rheumatism, vol. 39, No. 9 (supplement), p. S245, 1996.*
Wending et al. (Arthritis and Rheumatism, vol. 39, No. 9 (supplement), p. S245, 1996.*
Reece et al. (Arthritis and Rheumatism, vol. 39, No. 9 (supplement), p. S245, 1996.*

* cited by examiner

*Primary Examiner*—Janet Andres
(74) *Attorney, Agent, or Firm*—Scully, Scott, Murphy & Presser

(57) ABSTRACT

In accordance with the present invention, novel IL-16 antagonists, preferably peptides derived from CD4, have been isolated and synthesized. These peptides possess IL-16 antagonistic properties including the ability to selectively bind to IL-16 and inhibit IL-16-mediated biological activity. The peptides comprise specific portions of the native human CD4 receptor and variations thereof and therefore are non-immunogenic when administered to humans. The present invention also provides compositions containing at least one IL-16 antagonist peptide which can inhibit, suppress or cause the cessation of at least one IL-16-mediated biological activity in mammals, including humans. The present invention provides a method and composition for treating inflammation associated with disease states such as asthma, rheumatoid arthritis, inflammatory bowel disease (IBD) and systemic lupus (SLE) in mammals such as, for example, humans.

6 Claims, 15 Drawing Sheets

(2 of 15 Drawing Sheet(s) Filed in Color)

| Region | D1 | D2 | D3 | D4 |
|--------|-----|-----|-----|-----|
| Cat | 58% | 55% | 61% | 65% |
| Dog | 55% | 54% | 58% | 65% |
| Rabbit | 57% | 54% | 62% | 67% |
| Rat | 47% | 35% | 56% | 65% |
| Mouse | 55% | 48% | 58% | 63% |

(Human CD4 D4 domain aa 302-374)

NLTCEVWGPTSPKLMLSLKLENKEAKVSKREKAVWVLNPEAGMWQCLLSDSGQVL LESNIKVLPTWSTPVQPM
.LTCEV GPTSPK: . L: LK EN: EA: VS.: K. V V: .PE: G: WQCLLS : : : V  : : S. I : VL.:
TLTCEVMGPTSPKMRLTLKQENQEARVSEEGDKVVQVAPETG LWQCLLSEGDKVKMDSRIQVLS-RGVNQTVF (Murine CD4 D4 domain aa 301-372)

FIGURE 1

SEQUENCE LISTING

```
<160> NUMBER OF SEQ ID NOS: 41

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:IL-16
      antagonist peptide
<221> NAME/KEY: UNSURE
<222> LOCATION: (1)
<223> OTHER INFORMATION: Xaa can be any amino acid
<221> NAME/KEY: UNSURE
<222> LOCATION: (4)
<223> OTHER INFORMATION: Xaa can be any amino acid

<400> SEQUENCE: 1

Xaa Lys Lys Xaa
1
```

```
<210> SEQ ID NO 2
<211> LENGTH: 4
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 2

Cys Leu Leu Ser
  1

<210> SEQ ID NO 3
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide
<221> NAME/KEY: UNSURE
<222> LOCATION: (1)..(3)
<223> OTHER INFORMATION: Xaa can be any amino acid
<221> NAME/KEY: UNSURE
<222> LOCATION: (6)
<223> OTHER INFORMATION: Xaa can be any amino acid

<400> SEQUENCE: 3

Xaa Xaa Xaa Leu Leu Xaa
  1               5

<210> SEQ ID NO 4
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 4

Trp Gln Cys Leu Leu Ser
  1               5

<210> SEQ ID NO 5
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 5

Trp Gln Ala Leu Leu Ser
  1               5

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 6

Trp Ala Cys Leu Leu Ser
  1               5

<210> SEQ ID NO 7
<211> LENGTH: 6
<212> TYPE: PRT
```

-continued

```
<213> ORGANISM: Artificial Sequence
<220> FEATURE:
<223> OTHER INFORMATION: Description of Artificial Sequence:IL-16
      antagonist peptide

<400> SEQUENCE: 7

Trp Gln Cys Glu Leu Ser
  1               5

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide
<221> NAME/KEY: UNSURE
<222> LOCATION: (1)
<223> OTHER INFORMATION: Xaa can be any amino acid
<221> NAME/KEY: UNSURE
<222> LOCATION: (3)
<223> OTHER INFORMATION: Xaa can be any amino acid
<221> NAME/KEY: UNSURE
<222> LOCATION: (5)..(6)
<223> OTHER INFORMATION: Xaa can be any amino acid

<400> SEQUENCE: 8

Xaa Val Xaa Val Xaa Xaa
  1               5

<210> SEQ ID NO 9
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 9

Val Val Gln Val Val Ala
  1               5

<210> SEQ ID NO 10
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 10

Val Lys Gln Val Val Ala
  1               5

<210> SEQ ID NO 11
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 11

Val Val Gln Lys Val Ala
  1               5

<210> SEQ ID NO 12
<211> LENGTH: 16
<212> TYPE: PRT
```

```
<213> ORGANISM: Artificial Sequence
<220> FEATURE:
<223> OTHER INFORMATION: Description of Artificial Sequence:IL-16
      antagonist peptide

<400> SEQUENCE: 12

Gly Met Trp Gln Cys Leu Leu Ser Asp Ser Gly Gln Val Leu Leu Glu
 1               5                  10                  15

<210> SEQ ID NO 13
<211> LENGTH: 8
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 13

Gly Met Trp Gln Cys Leu Leu Ser
 1               5

<210> SEQ ID NO 14
<211> LENGTH: 12
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 14

Thr Gly Leu Trp Gln Cys Leu Leu Ser Glu Gly Asp
 1               5                  10

<210> SEQ ID NO 15
<211> LENGTH: 12
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 15

Val Ser Glu Glu Gln Lys Val Val Gln Val Val Ala
 1               5                  10

<210> SEQ ID NO 16
<211> LENGTH: 73
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 16

Asn Leu Thr Cys Glu Val Trp Gly Pro Thr Ser Pro Lys Leu Met Leu
 1               5                  10                  15

Ser Leu Lys Leu Glu Asn Lys Glu Ala Lys Val Ser Lys Arg Glu Lys
                20                  25                  30

Ala Val Trp Val Leu Asn Pro Glu Ala Gly Met Trp Gln Cys Leu Leu
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
65                  70
```

```
<210> SEQ ID NO 17
<211> LENGTH: 72
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 17

Thr Leu Thr Cys Glu Val Met Gly Pro Thr Ser Pro Lys Met Arg Leu
 1               5                  10                  15

Thr Leu Lys Gln Glu Asn Gln Glu Ala Arg Val Ser Glu Gln Lys
            20                  25                  30

Val Val Gln Val Val Ala Pro Glu Thr Gly Leu Trp Gln Cys Leu Leu
        35                  40                  45

Ser Glu Gly Asp Lys Val Lys Met Asp Ser Arg Ile Gln Val Leu Ser
    50                  55                  60

Arg Gly Val Asn Gln Thr Val Phe
 65                  70

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 18

Val Ser Glu Glu Gln Lys
 1               5

<210> SEQ ID NO 19
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 19

Val Val Gln Val Val Ala
 1               5

<210> SEQ ID NO 20
<211> LENGTH: 12
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 20

Leu Ser Lys Gln Lys Met Val Ser Arg Glu Gly Thr
 1               5                  10

<210> SEQ ID NO 21
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 21

Val Ala Pro Glu Thr Gly
```

<210> SEQ ID NO 22
<211> LENGTH: 6
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 22

Val Ile Gln Val Gln Ala
 1               5

<210> SEQ ID NO 23
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 23 gggggatgt ggaattgtct gctgagtgac                              30

<210> SEQ ID NO 24
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 24
gtcactcagc agacaattcc acatccccgc                             30

<210> SEQ ID NO 25
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 25
atgtggcagt gtatactgag tgactcggga                             30

<210> SEQ ID NO 26
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 26
tcccgagtca ctcagtatac actgccacat                             30

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 27

```
atgtggcagt gttcgctgag tgactcggga                                          30

<210> SEQ ID NO 28
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 28
tcccgagtca ctcagagcac actgccacat                                          30

<210> SEQ ID NO 29
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 29
atgtggcagt gtctgataag tgactcggga                                          30

<210> SEQ ID NO 30
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 30
tcccgactga cttatcagac actgccacat                                          30

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 31
atgtggcagt gtctgtcgag tgactcggga                                          30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence:
      Oligonucleotide primer

<400> SEQUENCE: 32
tcccgagtca ctagccagac actgccacat                                          30

<210> SEQ ID NO 33
<211> LENGTH: 73
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 33

Asn Leu Thr Cys Glu Val Trp Gly Pro Thr Ser Pro Lys Leu Met Leu
```

```
                1               5                   10                  15
Ser Leu Lys Leu Glu Asn Lys Glu Ala Lys Val Ser Lys Arg Glu Lys
                    20                  25                  30

Ala Val Trp Val Leu Asn Pro Glu Ala Gly Met Trp Asn Cys Leu Leu
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
65                  70

<210> SEQ ID NO 34
<211> LENGTH: 73
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 34

Asn Leu Thr Cys Glu Val Trp Gly Pro Thr Ser Pro Lys Leu Met Leu
 1               5                  10                  15

Ser Leu Lys Leu Glu Asn Lys Glu Ala Lys Val Ser Lys Arg Glu Lys
                    20                  25                  30

Ala Val Trp Val Leu Asn Pro Glu Ala Gly Met Trp Gln Cys Ser Leu
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
65                  70

<210> SEQ ID NO 35
<211> LENGTH: 73
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 35

Asn Leu Thr Cys Glu Val Trp Gly Pro Thr Ser Pro Lys Leu Met Leu
 1               5                  10                  15

Ser Leu Lys Leu Glu Asn Lys Glu Ala Lys Val Ser Lys Arg Glu Lys
                    20                  25                  30

Ala Val Trp Val Leu Asn Pro Glu Ala Gly Met Trp Gln Cys Leu Ser
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
65                  70

<210> SEQ ID NO 36
<211> LENGTH: 73
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 36

Asn Leu Thr Cys Glu Val Trp Gly Pro Thr Ser Pro Lys Leu Met Leu
 1               5                  10                  15
```

```
Ser Leu Lys Leu Glu Asn Lys Glu Ala Lys Val Ser Lys Arg Glu Lys
            20                  25                  30

Ala Val Trp Val Leu Asn Pro Glu Ala Gly Met Trp Gln Cys Ile Leu
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
 65                  70
```

<210> SEQ ID NO 37
<211> LENGTH: 73
<212> TYPE: PRT
<213> ORGANISM: Artificial Sequence
<220> FEATURE:
<223> OTHER INFORMATION: Description of Artificial Sequence:IL-16 antagonist peptide

<400> SEQUENCE: 37

```
Asn Leu Thr Cys Glu Val Trp Gly Pro Thr Ser Pro Lys Leu Met Leu
 1               5                  10                  15

Ser Leu Lys Leu Glu Asn Lys Glu Ala Lys Val Ser Lys Arg Glu Lys
            20                  25                  30

Ala Val Trp Val Leu Asn Pro Glu Ala Gly Met Trp Gln Cys Leu Ile
            35                  40                  45

Ser Asp Ser Gly Gln Val Leu Leu Glu Ser Asn Ile Lys Val Leu Pro
        50                  55                  60

Thr Trp Ser Thr Pro Val Gln Pro Met
 65                  70
```

<210> SEQ ID NO 38
<211> LENGTH: 16
<212> TYPE: PRT
<213> ORGANISM: Artificial Sequence
<220> FEATURE:
<223> OTHER INFORMATION: Description of Artificial Sequence:IL-16 antagonist peptide

<400> SEQUENCE: 38

```
Thr Ser Pro Lys Leu Met Leu Ser Leu Lys Leu Glu Asn Lys Glu Ala
 1               5                  10                  15
```

<210> SEQ ID NO 39
<211> LENGTH: 16
<212> TYPE: PRT
<213> ORGANISM: Artificial Sequence
<220> FEATURE:
<223> OTHER INFORMATION: Description of Artificial Sequence:IL-16 antagonist peptide

<400> SEQUENCE: 39

```
Lys Val Ser Lys Arg Glu Lys Ala Val Trp Val Leu Asn Pro Glu Ala
 1               5                  10                  15
```

<210> SEQ ID NO 40
<211> LENGTH: 8
<212> TYPE: PRT
<213> ORGANISM: Artificial Sequence
<220> FEATURE:
<223> OTHER INFORMATION: Description of Artificial Sequence:IL-16 antagonist peptide

<400> SEQUENCE: 40

```
Asp Ser Gly Gln Val Leu Leu Glu
```

```
<210> SEQ ID NO 41
<211> LENGTH: 4
<212> TYPE: PRT
<213> ORGANISM: Artificial Sequence
<220> FEATURE:
<223> OTHER INFORMATION: Description of Artificial Sequence:IL-16
      antagonist peptide

<400> SEQUENCE: 41

Gly Met Trp Gln
 1
```

IL-16 ANTAGONISTS

CROSS REFERENCE TO RELATED APPLICATIONS

The present application is a divisional of application Ser. No. 09/368,632 filed Aug. 5, 1999. +gi

GOVERNMENT SUPPORT

This invention was made with United States government support under grant number HL-32802 awarded by the National Institutes of Health. The United States government may have certain rights in the invention.

FIELD OF THE INVENTION

The present invention relates to protein and peptide chemistry. In particular, the present invention relates to the discovery and isolation of novel peptides whose sequences coincide with regions of the IL-16 receptor (CD4). The invention is also directed to the use of these novel peptides in the inhibition of IL-16-mediated biological activity.

BACKGROUND OF THE INVENTION

Interleukin-16 (IL-16) was first described in 1982 as lymphocyte chemoattractant factor (LCF; Center, et al., (1982) *J. Immunol.* 128: 2563–2568; Cruikshank, et al., (1982) *J. Immunol.* 128: 2569–2574). Subsequent studies showed that IL-16 is a multifunctional cytokine, selectively inducing the migration of CD4$^+$ T cells, eosinophils and monocytes. IL-16 also acts as a growth factor for resting CD4$^+$ T cells, promoting their entry into the G1 phase of the cell cycle, and inducing interleukin-2 receptor and major histocompatibility (MHC) class II protein expression on the cell surface. These activating functions are associated with intracellular signals including the synthesis of inositol trisphosphate (IP$_3$) and a transient increase of intracellular Ca$^{2+}$ concentration (reviewed in Cruikshank, et al. (1998) *International Reviews of Immunology* 16: 523–540).

CD4 is a ~55 kDa type 1 integral cell surface glycoprotein with four extracellular immunoglobulin-like extracellular domains (D1–D4), a single membrane-spanning region, and short intracytoplasmic tail which interacts with intracellular tyrosine kinases such as p56$^{lck}$. The extracellular domains appear to form two rigid structures consisting of D1D2 and D3D4, with a flexible connection between D2 and D3 (Brady, et al., (1993) *Science* 260: 979–983). The D1D2 domain interacts with MHC class II proteins and a high affinity (Kd ~10 nM) HIV-1 gp120 binding site maps to the N-terminus of the V1 region of CD4, overlapping with but distinct from the MHC class II binding site (Fleury, et al., (1991) *Cell* 66: 1037–1049). The seminal plasma gp17 binding site on CD4 is also located in the D1 domain, close to, but distinct from the gp120 binding site (Autiero, et al., (1997) *European Journal of Biochemistry* 245: 208–213).

CD4 is a receptor for IL-16. IL-16 induces chemotactic responses in CD4$^+$ but not CD4$^-$ T lymphocytes Berman, et al. (1985) 95:105–112. The T cell chemoattractant response to IL-16 is inhibited by co-incubation with Fab fragments of the anti-CD4 monoclonal antibody OKT 4, and the magnitude of the IL-16-induced cell migration by monocytes is directly proportional to the amount of CD4 expressed on the responding cells (Cruikshank, et al., (1987) *J. Immunol.* 138: 3817–3823). In addition, transfection of human CD4 confers IL-16-responsiveness to an otherwise unresponsive L3T4$^-$ murine hybridoma cell line as demonstrated by the induction of cell motility and rises in intracellular Ca$^{2+}$ and IP$_3$ which are inhibited by OKT4 Fab (Cruikshank, et al., (1991) *J. Immunol.* 146: 2928–2934).

Surface expression of CD4 is required for cells to respond to IL-16, and a direct interaction between IL-16 and CD4 was observed in co-immunoprecipitation experiments (Cruikshank, et al. (1998) *International Reviews of Immunology* 16: 523–540)). The CD4 ligand HIV-1 envelope glycoprotein gp120 and certain anti-CD4 antibodies mimic some of the bioactivities of IL-16 (Kornfeld, et al., (1988) *Nature* 335: 445–448; Ledbetter, et al., (1987) *Proc. Natl. Acad. Sci. USA* 84: 1384–1388; and Neudorf, et al., (1990) *Cell.Immunol.* 125: 301–314). Certain chemokine receptors are known to function as co-receptors with CD4 for HIV-1 infection (Feng, et al., (1996) *Science* 272: 872–877; Dragic, et al.,(1996) *Nature* 381: 667–673), but it is unknown whether co-receptors are utilized by IL-16. Another soluble CD4 ligand was reported by Autiero et al. (Autiero, et al., (1991) *Experimental Cell Research* 197: 268–271; Autiero, et al., (1995) *Eur. J. Immunol.* 25:1461–1464) who isolated a human seminal plasma glycoprotein, gp17, which binds to recombinant soluble CD4 coupled to Sepharose beads as well as to CD4$^+$ Jurkat cells. The physiological role of gp17 is presently unknown. Together, these findings indicate that CD4 is multi-functional receptor.

There is also direct physical evidence for an IL-16-CD4 interaction. IL-16 can be co-immunoprecipitated with recombinant soluble CD4, and rIL-16 partially displaces OKT4 bound to CD4 (Cruikshank, et al. (1994) *Proc. Natl. Acad. Sci. USA* 91: 5109–5113). Data from several laboratories indicate a high degree of sequence and functional homology for IL-16 across different animal species (Bannert, et al., (1998) *Immunogenetics* 47: 390–397; Keane, et al., (1998) *J. Immunol.* 160: 5945–5954; Leutenegger, et al., (1999) *Molecular cloning and expression of feline interleukin-16*, (UnPub)).

Human IL-16 induces chemotaxis of human, rat, and mouse CD4$^+$ T cells (Center, D. M. and Cruikshank, W. W. (1982) *J. Immunol.* 128: 2563–2568). Murine IL-16 also induces motility and interleukin-2 receptor (IL-2R)-expression in human and murine target cells. It is therefore believed that the site(s) on CD4 interacting with IL-16 are also likely to be conserved. Comparison of the predicted amino acid sequences of CD4 across several species indicates that the D4 domain of CD4 is critical for IL-16 bioactivity.

CD4 is also the major receptor for human immunodeficiency virus-1 (HIV-1), HIV -2, and human herpes virus-7 (Dalgleish, et al., (1984) *Nature* 312: 763–767; Klatzmann, et al. (1984) *Nature* 312: 767–768; Lusso, et al., (1994) *Proceedings of the National Academy of Sciences of the United States of America* 91, 3872–3876). Originally identified as a differentiation antigen on T lymphocytes, CD4 was later found to be expressed on a variety cell types including monocytes, macrophages, eosinophils, hematopoietic progenitor cells, neurons, and spermatoza (Foti, et al., (1995) *Journal of Laboratory & Clinical Medicine* 126: 233–239). Expression of CD4 by these non-lymphocytic cells indicates that it mediates functions independent of the T cell antigen receptor, although the nature of these putative functions remain to be defined. In addition to binding MHC class II proteins, it is believed that CD4 can serve as a receptor for other soluble ligands.

Until recently, no function has been attributed to the D4 domain of CD4. Wu et al. (Wu, et al., (1997) *Nature* 387: 527–530) reported the x-ray crystallographic structure of recombinant soluble human D3D4 which spontaneously dimerizes at high concentration in solution. Wu et al. found that domain 4 (D4) mediates CD4 dimerization, and that the interface between dimers involves D4 domains exclusively. At the center of the interface is a pair of conserved glutamine residues ($Gln^{345}$ and $Gln^{345'}$) separated by a hydrogen-bonding distance. In their model, the level of CD4 expression when evenly distributed on a cell surface (estimated at $\sim 10^{-5}$ M) would favor monomers. During antigen recognition, CD4 recruited by cooperative interactions at the cell-cell adhesion junction would lead to an increased local concentration favoring diner formation. Wu et al. proposed that CD4 dimerization-mediated trans autophosphorylation is required for CD4-associated kinase activation, and subsequent intracellular signaling. In support of this model, Satoh et al. (Satoh, et al., (1996) *Biochemical & Biophysical Research Communications* 224: 438–443) found that D4-based peptides were capable of inhibiting a mixed lymphocyte reaction (MLR). The activity of these peptides was postulated to result from competitive binding to CD4, thus inhibiting CD4 dimerization.

Comparison of the human CD4 amino acid sequence with that of several different species revealed that immunoglobulin-like domain 4 (D4) is the most conserved extracellular region. A comparison of the amino acid sequence of the human CD4 D4 domain with the CD4 D4 domain of mice reveals that 37 out of 73 amino acids are identical. Mouse and human D4 regions have an amino acid sequence homology of approximately 63% as determined by the method of Lipman et al., (1985) *Science* 227: 1435–1441.

As it is established that IL-16 is a key modulator of immune and inflammatory diseases, it would be desirable to identify IL-16 antagonists, i.e., substances capable of blocking or interrupting the activity of IL-16, for use in anti-inflammatory compositions in the treatment of, e.g., asthma, rheumatoid arthritis or inflammatory bowel disease. Such compositions may also prove to be more advantageous over presently available NSAIDs, steroid based anti-inflammatory drugs and cytotoxic drugs which often have severe side effects with the continued usage that is required for chronic inflammatory diseases.

SUMMARY OF THE INVENTION

One embodiment of the present invention is directed to IL-16 antagonists.

Another embodiment of the present invention is directed to IL-16 antagonist peptides.

In accordance with the present invention, novel IL-16 antagonist peptides derived from or corresponding to the CD4 receptor have been isolated and synthesized. These peptides possess IL-16 antagonistic properties including the ability to selectively bind to IL-16 and inhibit IL-16-mediated biological activity which, for example, is associated with certain inflammatory responses in mammals. The peptides of the present invention preferably correspond to specific portions of the native human CD4 receptor and include variations thereof, and therefore are non-immunogenic when administered to humans.

The present invention also provides methods and compositions for treating IL-16 mediated disorders such as the inflammation associated with asthma, rheumatoid arthritis, inflammatory bowel disease (IBD) and systemic lupus (SLE). The present invention provides specific compositions containing at least one IL-16 antagonist peptide which inhibits, suppresses or causes the cessation of at least one IL-16-mediated biological activity in a mammal, and preferably humans.

The IL-16 antagonist peptides of the present invention are at least 4 amino acids in length and substantially correspond to the amino acids of the D4 domain of human or murine CD4 surrounding the Leu-Leu motif, i.e., $L^{348}$–$L^{349}$ of human CD4 D4 or $L^{347}$–$L^{348}$ of murine CD4 D4.

A preferred IL-16 antagonist peptide of the present invention is a tetrameric peptide having the sequence $Xaa_1$-L-L-$Xaa_2$, wherein $Xaa_1$ and $Xaa_2$ can be any amino acid.

Preferably, $Xaa_1$ and $Xaa_2$ are those amino acids found in the native sequence of a mammalian CD4. For example, $Xaa_1$ can be Cys (human or murine) and $Xaa_2$ can be Ser (human or murine). Homologs and analogs of this tetrameric peptide are also IL-16 contemplated by the present invention.

More preferably, $Xaa_1LLXaa_2$ is a tetrameric peptide identical to the native sequence of a human CD4. For example, CLLS (SEQ ID NO:2) is most preferred.

Another preferred IL-16 antagonist peptide of the present invention is a six-residue peptide having the sequence of $Xaa_1$-$Xaa_2$-$Xaa_3$-Leu-Leu-$Xaa_4$, wherein $Xaa_1$-$Xaa_4$ can be any amino acid (SEQ ID NO:3).

Preferably, $Xaa_{1-4}$ are those amino acids found in the native sequence of a mammalian (e.g. murine and human) CD4 at the relevant positions. For example, $Xaa_1$ can be Trp, $Xaa_2$ can be Gln or Ala, $Xaa_3$ can be Cys or Ala and $Xaa_4$ can be Ser.

Even more preferably, $Xaa_1$-$Xaa_2$-$Xaa_3$-L-L-$Xaa_4$ is a 6-mer identical to the native sequence of human or murine CD4. An example of such a 6-mer includes SEQ ID NO:4 WQCLLS. Homologs and analogs of this 6-mer are also contemplated by the present invention. Examples of such homologs and analogs include: WQALLS (SEQ ID NO:5), WACLLS (SEQ ID NO:6) and WQCELS (SEQ ID NO:7).

Still another preferred IL-16 antagonist peptide of the present invention is a 6-mer having the sequence of $Xaa_1$-Val-$Xaa_2$-Val-$Xaa_3$-$Xaa_4$ wherein $Xaa_{1-4}$ can be any amino acid (SEQ ID NO:8).

Preferably, $Xaa_{1-4}$ are those amino acids found in the native sequence of a mammalian (e.g. murine and human) CD4 at the relevant positions. For example, $Xaa_1$ can be Val, $Xaa_2$ can be Gln, $Xaa_3$ can be Val and $Xaa_4$ can be Ala.

Even more preferably, $Xaa_1$-Val-$Xaa_2$-Val-$Xaa_3$-$Xaa_4$ is a 6-mer identical to the native sequence of human or murine CD4. An example of such a 6-mer includes SEQ ID NO:9 VVQVVA. Homologs and analogs of this 6-mer are also contemplated by the present invention. Examples of such homologs and analogs include: VKQVVA (SEQ ID NO:10) and VVQKVA (SEQ ID NO:11).

Further, according to the present invention an IL-16 antagonist peptide can be longer than a tetrameric and a 6-mer and composed of up to about 75 amino acids, as long as the antagonist peptide contains as part of the peptide, one or more of the tetrameric or 6-mer sequences described hereinabove, i.e. $Xaa_1LLXaa_2$, $Xaa_1$-$Xaa_2$-$Xaa_3$-L-L-$Xaa_4$ or $Xaa_1$-V-$Xaa_2$-V-$Xaa_3$-$Xaa_4$, and preferably $Xaa_1LLXaa_2$. Preferably, the antagonist peptide contains less than about 32 amino acids and more preferably less than about 16 amino acids.

Preferred antagonist peptides include those having sequences which coincide with the native sequence of a CD4 starting from $Asn^{302}$ for human CD4, or the corresponding positions of other mammalian CD4 molecules, such as, for example $Thr^{301}$ for murine CD4. Examples of such "longer" peptides include GMWQCLLSDSGQVLLE (SEQ ID NO:12), GMWQCLLS (SEQ ID NO:13), TGLWQCLL- SEGD (SEQ ID NO:14), VSEEQKVVQVVA (SEQ ID NO:15), NLTCEVWGPTSPKLMLSLKLEN-KEAKVSKREKAVWVLNPEAGMWQCLLSDSGQVLLE SNIKVLPTWSTPVQPM (SEQ ID NO:16) and TLT-CEVMGPTSPKMRLTLKQENQEARVSE-EQKVVQVVAPETGLWQCLLSEGDKVKMD SRIQV-LSRGVNQTVF (SEQ ID NO:17).

In the amino acid sequences defined herein, the numbering of the amino acid residues corresponds to the numbering of amino acid residues in the amino acid sequence for human T-cell surface glycoprotein T4 mRNA as provided in Maddon, et al. (1985) Cell 42:93–104 (incorporated herein by reference). Homologous peptides are derived from the homologous regions of other CD4 polypeptides, such as mouse CD4, aligned in sequence for maximal homology.

In one embodiment, the amino acid sequence of the IL-16 antagonist peptide substantially corresponds to amino acids 347–350 (CLLS) of the human CD4 domain 4 (D4) (SEQ ID NO:2).

In another embodiment of the present invention, the amino acid sequence of the IL-16 antagonist peptide substantially corresponds to amino acids 343–358 (GMWQCLLSDSGQVLLE) of the human CD4 domain 4 (D4) (SEQ ID NO:12).

In still another embodiment of the present invention, the amino acid sequence of the IL-16 antagonist peptide substantially corresponds to amino acids 343–350 (GMWQCLLS) of the human CD4 domain (SEQ ID NO:13).

In another embodiment, the amino acid sequence of the IL-16 antagonist peptide substantially corresponds to amino acids 344–349 (WQCLLS) of the mouse CD4 domain 4 (D4). (SEQ ID NO:4).

In still another embodiment, the amino acid sequences of the IL-16 antagonist peptides substantially correspond to amino acid residues 333–338 of the mouse CD4 D4 region (SEQ ID NO:9).

In yet another embodiment, the amino acid sequences of the IL-16 antagonist peptides substantially correspond to amino acid residues 301–372 (TLTCEVMGPTSPKMRLTLKQENQEARVSEEQKVV QVVAPETGLWQCLLSEGDKVKM DSRIQVLSRGVNQTVF) of the mouse CD4 D4 (SEQ ID NO:17).

In still yet another embodiment, the amino acid sequences of the IL-16 antagonist peptides substantially correspond to amino acid residues 327–338 (VSEEQKVVQVVA) of the mouse CD4 D4 (SEQ ID NO:15).

In another embodiment, the amino acid sequences of the IL-16 antagonist peptides substantially correspond to amino acid residues 341–352 (TGLWQCLLSEGD) of the mouse CD4 D4 (SEQ ID NO:14).

In still yet another embodiment, the amino acid sequences of the IL-16 antagonist peptides substantially correspond to amino acid residues 302–374 (NLTCEVWGPTSPKLMLSLKLENKEAKVSKREKAV WVLNPEAGMWQCLLSDSGQVLL ESNIKVLPTWSTPVQPM) of the human CD4 D4 (SEQ ID NO:16).

Homologs, analogs and fragments of these peptides are also contemplated by the present invention as IL-16 peptide antagonists which maintain IL-16 antagonist activity in a mammal, particularly humans.

Another aspect of the present invention provides methods of interfering with, blocking or otherwise preventing the interaction or binding of IL-16 with an IL-16 receptor by employing the IL-16 antagonists contemplated by the present invention.

The present invention also provides compositions for the treatment of IL-16-mediated disorders such as asthma, arthritis, inflammatory bowel disease (IBD), systemic lupus erythmatous (SLE), multiple sclerosis, Graves opthalmopathy, atopic rhinitis, atopic dermatitis, bullous phemphigoid, or other CD4$^+$ cell mediated diseases, in animals, including humans and includes methods of treating such disorders. The compositions include at least one of the IL-16 antagonists, preferably at least the IL-16 peptide antagonist according to the present invention, admixed with a pharmaceutically acceptable carrier.

Nucleic acid molecules coding for any of the above IL-16 antagonist peptides of the present invention, expression vectors which include any of such nucleic acid molecules, as well as related host cells containing such nucleotide sequences or vectors, are also contemplated by the present invention.

Still another embodiment of the present invention is directed to antibodies raised against the IL-16 antagonist peptides of the present invention.

Preferably, the antibodies of the present invention are raised against those IL-16 antagonist peptides whose sequences coincide with the corresponding sequences of a mammalian IL-16 protein, which antibodies can antagonize or neutralize the activity of IL-16. Both polyclonal antibodies and monoclonal antibodies are contemplated by the present invention.

These and other embodiments of the invention will be readily apparent to those of ordinary skill in view of the disclosure herein.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1 Provides a CD4 sequence comparison. Each of the four extra-cellular immunoglobulin-like domains (D1–D4) of the predicted cat, dog, rabbit, rat, and mouse CD4 amino acid sequences were compared with the human CD4 protein sequence by the method of Lipman and Pearson. The similarity index of each non-human species in comparison with the corresponding domain of human CD4 is shown in the table. The predicted amino acid sequences of the human D4 domain (top row) and murine D4 domain (bottom row) are displayed below the table. Conserved residues are indicated (middle row), with colons representing conservative substitutions, periods representing semi-conservative substitution, and blank spaces representing non-conservative substitutions. Genbank accession numbers for the cDNA sequences from which this information was prepared include: human (M12807), mouse (X04836), cat (AB000483), dog (L06130), rabbit (M92840), and rat (M15768).

DETAILED DESCRIPTION OF THE INVENTION

Figure 2:
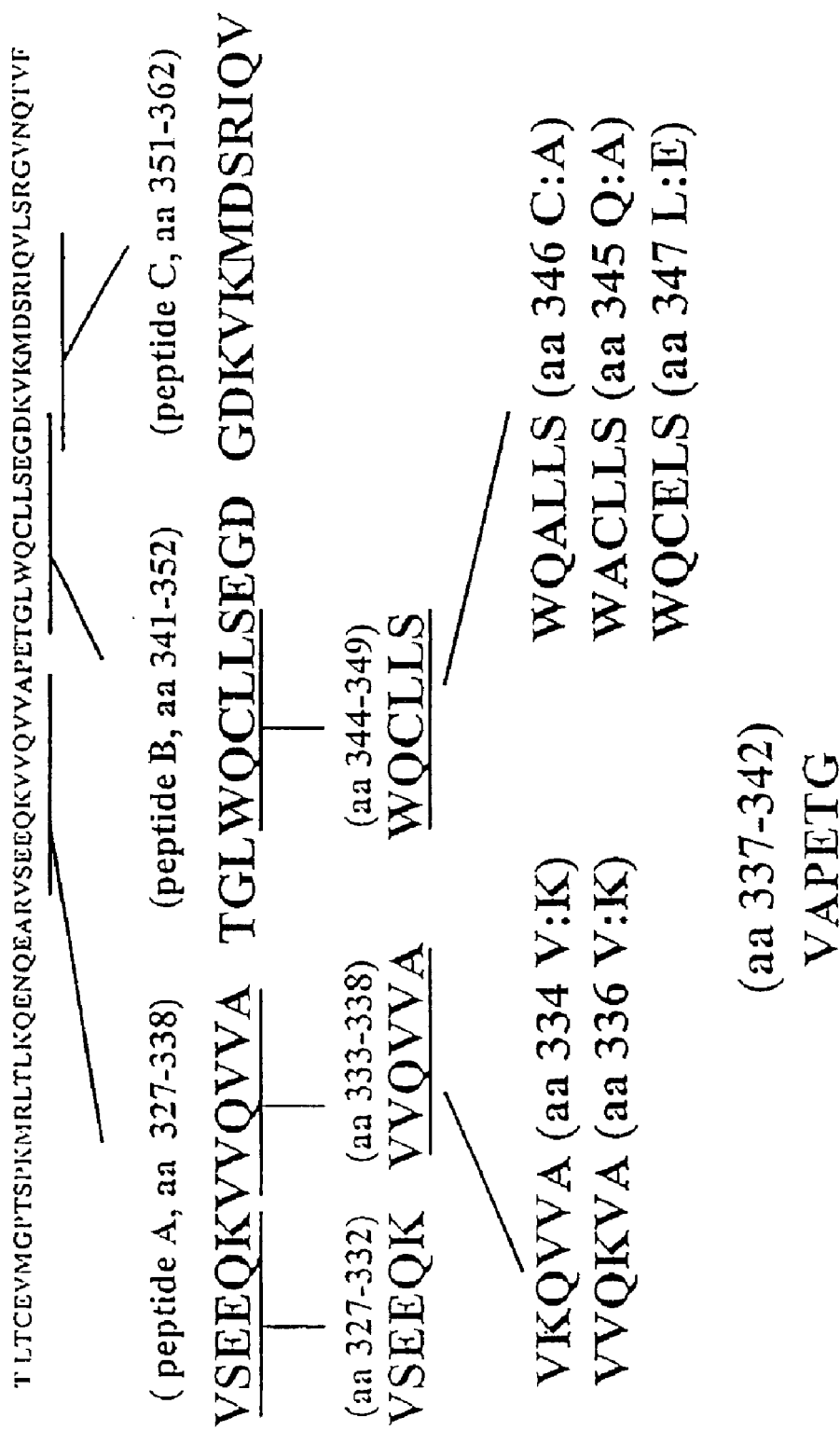
FIG. 2 Provides synthetic oligopeptides prepared for IL-16 inhibition experiments. Among other D4 sequences, the two 12-residue peptides designated A and B and the 6-residue peptide designated C were uniquely found to inhibit IL-16 (below). The residues within peptide A and peptide B required for IL-16 inhibition were tested by using the 6-residue peptides shown. These include native sequences and peptides with non-conservative amino acid substitutions.

The present invention is directed to Interleukin-16 (IL-16) antagonists. By "IL-16 antagonist" is meant any molecule that inhibits, suppresses or causes the cessation of at least one IL-16-mediated biological activity by, e.g., interfering with, blocking or otherwise preventing the interaction or binding of IL-16 to an IL-16 receptor, e.g., the CD4 receptor.

More specifically, the present invention provides IL-16 antagonist peptides which substantially correspond to amino acid sequences found in specific portions of the CD4 receptor. The peptides of the present invention correspond to sequences found in the immunoglobulin-like domain 4 (D4) extracellular region of the CD4 and can inhibit the activity of IL-16. Surprisingly, the present inventors have found that such IL-16 inhibiting peptides can be as short as 4 amino acids in length.

As used herein, "peptide" refers to a linear series of amino acid residues linked to one another by peptide bonds between the alpha-amino and carboxy groups of adjacent amino acid residues. The term "synthetic peptide" is intended to refer to a chemically derived chain of amino acid residues linked together by peptide bonds. The term "synthetic peptide" is also intended to refer to recombinantly produced peptides in accordance with the present invention.

The sequences of the peptides of the present invention are derived from and/or correspond to the amino acid sequence of murine CD4 domain 4, however, homologous peptides derived from human, rat and other mammalian CD4 sequences are also encompassed by the invention. It is known that mouse and human CD4 are substantially homologous in amino acid sequence, with the homology being about 63%. It is known that IL-16 is cross reactive between species Keane, et al. (1998) *J. Immunol.* 160:5945.

By "IL-16 antagonist peptide" is meant a peptide that inhibits, suppresses or causes the cessation of at least one IL-16-mediated biological activity by e.g., binding to IL-16, interfering with, or preventing the binding of IL-16 to the CD4 receptor. An IL-16 antagonist functions in two ways. The antagonist can bind to or sequester IL-16 with sufficient affinity and specificity to substantially interfere with, block or otherwise prevent binding of IL-16 to an IL-16 receptor, thereby inhibiting, suppressing or causing the cessation of at least one IL-16-mediated biological activity, such as T-cells chemotaxis, for example. This type of IL-16 antagonist, also termed a "sequestering antagonist" is a specific feature of this invention. Alternatively, an IL-16 antagonist can compete with IL-16 for the cell surface receptor thereby interfering with, blocking or otherwise preventing the binding of IL-16 to an IL-16 receptor. This type of antagonist, e.g., which binds the receptor but does not trigger signal transduction, is also referred to herein as a "competitive antagonist". The contemplated "competitive antagonists" are, more specifically, described in commonly owned co-pending application Ser. No. 09/368,632, filed on Aug. 5, 1999, entitled "IL-16 Antagonists", the disclosure of which is incorporated herein by reference. The peptide antagonists are useful in the therapy of immunoinflammatory responses. Additionally, analogs, homologs and fragments of the novel peptides provided herein are included within the scope of the term "IL-16 antagonist peptide".

According to the present invention, preferred IL-16 antagonists include peptides (referred to herein as "IL-16 antagonist peptides") and antibodies.

By "IL-16-mediated biological activity" as used herein is meant chemotaxis of CD4+ cells such as CD4+ T cells, inhibition of retroviral replication (such as inhibition of HIV and SIV in infected PBMCs), upregulation of IL-2R on CD4+ T cells, synergy with IL-2 for CD4$^+$ T cell proliferation, induction of RAG-1 and RAG-2 expression in CD4$^+$ pro-B cells, and inhibition of Mixed Lymphocyte Reaction (MLR). These IL-16 mediated biological activities can be determined using the assays described by Cruikshank et al. (*Proc. Natl. Acad. Sci. USA* 91: 5109–5113, 1994); Maciaszek et al. (*J. Immunol.* 158:5, 1997), Zhou, et al. (*Nature Medicine* 3:659, 1997) and Baier et al. (*Nature* 378:563, 1995); Parada et al. (*J. Immunol.* 160:2115, 1998); Szabo et al. (*J. Immunol.*, 161:2248, 1998); and Theodore et al. (*J. Immunol.* 157:1958, 1996), respectively. The teachings of these references are incorporated herein by reference.

By "homologs" is meant the corresponding peptides from CD4 proteins of other mammalian species substantially homologous at the overall protein (i.e., mature protein) level to human or murine CD4, so long as such homologous peptides retain the IL-16 antagonist activity.

By "analogs" is meant peptides which differ by one or more amino acid alterations, which alterations, e.g., substitutions, additions or deletions of amino acid residues, do not abolish the IL-16 antagonist properties of the relevant peptides.

According to the present invention, an IL-16 antagonist peptide is at least 4 amino acids in length and substantially corresponds to the amino acids comprising the D4 domain of human or murine CD4 surrounding the Leu-Leu motif, i.e., $L^{348}$–$L^{349}$ of human CD4 D4 or $L^{347}$–$L^{348}$ of murine CD4 D4.

Thus, an analog may comprise a peptide having a substantially identical amino acid sequence to a peptide provided herein and in which one or more amino acid residues have been conservatively or non-conservatively substituted. Examples of conservative substitutions include the substitution of a non-polar (hydrophobic) residue such as isoleucine, valine, leucine or methionine for another. Likewise, the present invention contemplates the substitution of one polar (hydrophilic) residue such as between arginine and lysine, between glutamine and asparagine, and between glycine and serine. Additionally, the substitution of a basic residue such as lysine, arginine or histidine for another or the substitution of one acidic residue such as aspartic acid or glutamic acid for another is also contemplated. Examples of non-conservative substitutions include the substitution of a non-polar (hydrophobic) residue such as isoleucine, valine, leucine, alanine, methionine for a polar (hydrophilic) residues such as cyteine, glutamine, glutamic acid, lysine and/or a polar residue for a non-polar residue.

The phrase "conservative substitution" also includes the use of chemically derivatized residues in place of a non-derivatized residues as long as the peptide retains the requisite IL-16 antagonist, inhibition or suppression properties as conventionally measured by the MLR assay (Theodore et al (1996) J. Immunol. 157:1958–1964). Analogs also include the presence of additional amino acids or the deletion of one or more amino acids which do not affect IL-16-mediated biological activity. For example, analogs of the subject peptides can contain an N- or C-terminal cysteine, by which, if desired, the peptide may be covalently attached to a carrier protein, e.g., albumin. Such attachment, it is believed, will minimize clearing of the peptide from the blood and also prevent proteolysis of the peptides. In addition, for purposes of the present invention, peptides containing D-amino acids in place of L-amino acids are also included in the term "conservative substitution." The presence of such D-isomers can help minimize proteolytic activity and clearing of the peptide.

A preferred IL-16 antagonist peptide of the present invention is a tetrameric peptide having the sequence Xaa$_1$-L-L-Xaa$_2$ (SEQ ID NO:1), wherein Xaa$_1$ and Xaa$_2$ can be any amino acid which includes A=Ala=Alanine
R=Arg=Arginine
N=Asn=Asparagine
D=Asp=Aspartic acid B=Asx=Asparagine or aspartic acid
C=Cys=Cysteine
Q=Gln=Glutamine
E=Glu=Glutamic acid
Z=Glx=Glutamine or Glutamic acid
G=Gly=Glycine
H=His=Histidine
I=Ile=Isoleucine
L=Leu=Leucine
K=Lys=Lysine
F=Phe=Phenylalanine
P=Pro=Proline
S=Ser=Serine
T=Thr=Threonine
W=Trp=Tryptophan
Y=Tyr=Tyrosine
V=Val=Valine Preferably, $Xaa_1$ and $Xaa_2$ are those amino acids found in the native sequence of a mammalian CD4. For example $Xaa_1$ can be Cys (human or murine) and $Xaa_2$ can be Ser (human or murine). Homologs and analogs of this tetrameric peptide are also contemplated by the present invention.

More preferably, $Xaa_1LLXaa_2$ is a tetrameric peptide identical to the native sequence of a human CD4. For example, CLLS (SEQ ID NO:2) is most preferred.

Another preferred IL-16 antagonist peptide of the present invention is a six-residue peptide having the sequence of $Xaa_1-Xaa_2-Xaa_3$-Leu-Leu-$Xaa_4$ (SEQ ID NO:3), wherein $Xaa_{1-4}$ can be any amino acid.

Preferably, $Xaa_{1-4}$ are those amino acids found in the native sequence of a mammalian (e.g. murine and human) CD4 at the relevant position. For example, $Xaa_1$ can be Trp, $Xaa_2$ can be Gln or Ala, $Xaa_3$ can be Cys or Ala and $Xaa_4$ can be Ser.

Even more preferably, $Xaa_1-Xaa_2-Xaa_3$-L-L-$Xaa_4$ is a 6-mer identical to the native sequence of human or murine CD4. An example of such a 6-mer includes SEQ ID NO:4 WQCLLS. Homologs and analogs of this 6-mer which maintain IL-16 antagonist activity are also contemplated by the present invention. Examples of such homologs and analogs include: WQALLS (SEQ ID NO:5) WACLLS (SEQ ID NO:6) and WQCELS (SEQ ID NO:7).

Still another preferred IL-16 antagonist peptide of the present invention is a 6-mer having the sequence of $Xaa_1$-Val-$Xaa_2$-Val-$Xaa_3$-$Xaa_4$ (SEQ ID NO:8) wherein $Xaa_{1-4}$ can be any amino acid.

Preferably, $Xaa_{1-4}$ are those amino acids found in the native sequence of a mammalian (e.g. murine and human) CD4 at the relevant position. For example, $Xaa_1$ can be Val, $Xaa_2$ can be Gln, $Xaa_3$ can be Val and $Xaa_4$ can be Ala.

Even more preferably, $Xaa_1$-Val-$Xaa_2$-Val-$Xaa_3$-$Xaa_4$ is a 6-mer identical to the native sequence of human or murine CD4. An example of such a 6-mer includes SEQ ID NO:9 VVQVVA. Homologs and analogs of this 6-mer are also contemplated by the present invention. Examples of such homologs and analogs include: VKQVVA (SEQ ID NO:10) and VVQKVA (SEQ ID NO:11).

Further, according to the present invention an IL-16 antagonist peptide can be longer than a tetrameric and a 6-mer and composed of up to about 75 amino acids, as long as the antagonist peptide contains as part of the peptide, one or more of the tetrameric or 6-mer sequences described hereinabove, i.e. $Xaa_1LLXaa_2$, $Xaa_1-Xaa_2-Xaa_3$-L-L-$Xaa_4$ or $Xaa_1$-V-$Xaa_2$-V-$Xaa_3$-$Xaa_4$, and preferably $Xaa_1LLXaa_2$. Preferably, the antagonist peptide contains less than about 32 amino acids and more preferably less than about 16 amino acids.

Preferred antagonist peptides include those having sequences which coincide with the native sequence of a CD4 starting from $Asn^{302}$ for human CD4, or the corresponding positions of other mammalian CD4 molecules, such as, for example $Thr^{301}$ for murine CD4. Examples of such "longer" peptides include GMWQCLLSDSGQVLLE (SEQ ID NO:12), GMWQCLLS (SEQ ID NO:13), TGLWQCLLSEGD (SEQ ID NO:14), VSEEQKVVQVVA (SEQ ID NO:15), NLTCEVWGPTSPKLMLSLKLENKEAKVSKREKAVWVLNPEAGMWQCLLSDSGQVLLESNIKVLPTWSTPVQPM (SEQ ID NO:16) and TLTCEVMGPTSPKMRLTLKQENQEARVSEEQKVVQVVAPETGLWQCLLSEGDKVKMD SRIQVLSRGVNQTVF (SEQ ID NO:17) and homologs and analogs of the "longer" peptides.

As used herein, the term "substantially corresponds" is meant the degree of amino acid homology of at least about 60% homology, preferably at least about 70%, and more preferably at least about 75%, which degree is the similarity index calculated using the Lipman-Pearson Protein Alignment program with the following choice of parameters: Ktuple=2, Gap penalty=4, and Gap Length Penalty=12.

The term "fragment" refers to any subject peptide having an amino acid sequence shorter than that of any peptide depicted in SEQ ID NOS: 12–17 which contains at least one tetramer or hexamer of SEQ ID NO: 1, SEQ ID NO: 3, SEQ ID NO: 8 (i.e., $Xaa_1LLXaa_2$, $Xaa_1-Xaa_2-Xaa_3$-L-L-$Xaa_4$ or $Xaa_1$-V-$Xaa_2$-V-$Xaa_3$-$Xaa_4$), and which fragment retains the IL-16 mediated antagonist activity of the subject peptides.

The practice of the present invention employs, unless otherwise indicated, conventional techniques of synthetic organic chemistry, protein chemistry, molecular biology, microbiology, and recombinant DNA technology, which are well within the skill of the art. These techniques are applied in connection with peptide synthesis, recombinant production of peptides and peptide mutagenesis, for example. Such techniques are explained fully in the literature. See e.g., Scopes, R. K., *Protein Purification Principles and Practices*, 2d ed. (Springer-Verlag. 1987), *Methods in Enzymology* (M. Deutscher, ed., Academic Press, Inc. 1990), Sambrook, et al., *Molecular Cloning: A laboratory Manual*, 2d ed., (Cold Spring Harbor Press, Cold Spring Harbor, N.Y., 1989), *Handbook of Experimental Immunology*, Vols. I–IV (D. M. Weir and C. C. Blackwell, eds., 1986, Blackwell Scientific Publications), House, *Modern Synthetic Reactions*, 2d ed., (Benjamin/Cummings, Menlo Park, Calif., 1972).

The peptides of the present invention, homologs, analogs and fragments thereof may be synthesized by a number of known techniques. For example, the peptides may be prepared using the solid-phase synthetic technique initially described by Merrifield, in J. Am. Chem. Soc. 85:2149–2154 (1963). Other peptide synthesis techniques may be found in M. Bodanszky, et al. *Peptide Synthesis*, John Wiley & Sons, 2d Ed., (1976) and other references readily available to those skilled in the art. A summary of polypeptide synthesis techniques can be found in J. Stuart and J. D. Young, *Solid Phase Peptide Synthesis*, Pierce Chemical Company, Rockford, Ill., (1984). Peptides may also be synthesized by solution methods as described in *The Proteins*, Vol. II. 3d Ed., Neurath, H. et al., Eds., p. 105–237, Academic Press, New York, N.Y. (1976). Appropriate protective groups for use in different peptide syntheses are described in the above-mentioned texts as well as in J. F. W. McOmie, *Protective Groups in Organic Chemistry*, Plenum Press, New York, N.Y. (1973). The peptides of the present invention can also be prepared by chemical or enzymatic cleavage from larger portions of the CD4 molecule or from the entire CD4 molecule.

Additionally, the peptides of the present invention may also be prepared by recombinant DNA techniques (see e.g. *Current Protocols in Molecular Cloning* Ausubel et al., 1995, John Wiley & Sons, New York); Sambrook et al., 1989, *Molecular Cloning: A Laboratory Manual*, Second Edition, Cold Spring Harbor Laboratory Press, New York; Coligan et al. *Current Protocols in Immunology*, John Wiley & Sons Inc., New York, N.Y. (1994)). The skilled artisan understands that any of a wide variety of expression systems can be used to provide the recombinant peptides of the present invention. The precise host cell used is not critical to the invention. The IL-16 antagonist peptides can be produced in a prokaryotic host (e.g. *E. coli*), or in a eukaryotic host (e.g., *S. cerevisiae* or mammalian cells, e.g. COS1, CHO, NIH3T3, and JEG3 cells, or in the cells of an arthropod, e.g. *S. frugiperda*). Such cells are available from e.g. the American Type Culture Collection, Manassas, VA. The method of transfection and the choice of expression vehicle will depend on the host system selected. Transformation and transfection methods are described, e.g. in Sambrook et al. supra; expression vehicles can be chosen from those provided e.g. in *Cloning Vectors: A Laboratory Manual* P. H. Powels et al (1985), Supp. 1987.

For most of the amino acids used to build proteins, more than one coding nucleotide triplet (codon) can code for a particular amino acid residue. This property of the genetic code is known as redundancy. Therefore, a number of different nucleotide sequences can code for a particular subject IL-16 antagonist peptide. The present invention also contemplates a deoxyribonucleic acid (DNA) molecule or segment that defines a gene coding for, i.e., capable of expressing, a subject peptide or a subject chimeric peptide from which a peptide of the present invention may be enzymatically or chemically cleaved.

DNA molecules that encode peptides of the present invention can be synthesized by chemical techniques, for example, the phosphotriester method of Matteuccie, et al., J. Am. Chem. Soc. 103:3185(1981). Using a chemical DNA synthesis technique, desired modifications in the peptide sequence can be made by making substitutions for bases which code for the native amino acid sequence. Ribonucleic acid equivalents of the above described DNA molecules may also be used.

A nucleic acid molecule comprising a vector capable of replication and expression of a DNA molecule defining coding sequence for a subject polypeptide or subject chimeric polypeptide is also contemplated.

The peptides of the present invention are chemically synthesized by conventional techniques such as the Merrifield solid phase technique. In general, the method comprises the sequential addition of one or more amino acid residues to a growing peptide chain. Normally, either the amino or carboxyl group of the first amino acid residue is protected by a suitable, selectively removable protecting group. A different, selectively removable protecting group is utilized for amino acids containing a reactive side group such as lysine.

A preferred method of solid phase synthesis entails attaching the protected or derivatized amino acid to an inert solid support through its unprotected carboxyl or amino group. The protecting group of the amino or carboxyl group is then selectively removed and the next amino acid in the sequence having the complementary (amino or carboxyl) group suitably protected is admixed and reacted under conditions suitable for forming the amide linkage with the residue already attached to the solid support. The protecting group of the amino carboxyl group is then removed from this newly added amino acid residue, and the next amino acid (suitably protected) is then added, and so forth. After all the desired amino acids have been linked in the proper sequence, any remaining terminal and side group protecting groups including the solid support are removed sequentially or concurrently to yield the final peptide. The lyophilized oligopeptides are resuspended in double distilled $H_2O$ at 2 mg/ml as stock solutions and subsequently diluted in M199-HPS for experiments.

Peptides SEQ ID NOS:1–22 and 33–41 have the following sequences:

| | |
|---|---|
| $Xaa_1$-L-L-$Xaa_2$ | SEQ ID NO:1 |
| CLLS | SEQ ID NO:2 |
| $Xaa_1$-$Xaa_2$-$Xaa_3$-L-L-$Xaa_4$ | SEQ ID NO:3 |
| WQCLLS | SEQ ID NO:4 |
| WQALLLS | SEQ ID NO:5 |
| WACLLS | SEQ ID NO:6 |
| WQCELS | SEQ ID NO:7 |
| $Xaa_1$-VaL-$Xaa_2$-Val-$Xaa_3$-$Xaa_4$ | SEQ ID NO:8 |
| VVQVVA | SEQ ID NO:9 |
| VKQVVA | SEQ ID NO:10 |
| VVQKVA | SEQ ID NO:11 |
| GMWQCLLSDSGQVLLE | SEQ ID NO:12 |
| GMWQCLLS | SEQ ID NO:13 |
| TGLWQCLLSEGD | SEQ ID NO:14 |
| VSEEQKVVQVVA | SEQ ID NO:15 |
| NLTCEVWGPTSPKLMLSLKLENKEAKVSKREKAVWVL NPEAGMWQCLLSDSGQVLLESNIKVLPTWSTPVQPM | SEQ ID NO:16 |
| TLTCEVMGPTSPKMRLTLKQENQEARVSEEQKVVQVV APETGLWQCLLSEGDKVKMDSRIQVLSRGVNQTVF | SEQ ID NO:17 |
| VSEEQK | SEQ ID NO:18 |
| VVQVVA | SEQ ID NO:19 |
| LSKQKMVSREGT | SEQ ID NO:20 |
| VAPETG | SEQ ID NO:21 |
| VIQVQA | SEQ ID NO:22 |
| gggggatgtggaattgtctgctgagtgac | SEQ ID NO:23 |
| gtcactcagcagacaattccacatccccgc | SEQ ID NO:24 |
| atgtggcagtgtatactgagtgactcggga | SEQ ID NO:25 |
| tcccgagtcactcagtatacactgccacat | SEQ ID NO:26 |
| atgtggcagtgttcgctgagtgactcggga | SEQ ID NO:27 |

```
                                              -continued
tcccgagtcactcagagcacactgccacat                          SEQ ID NO:28 atgtggcagtgtctgataagtgactcggga                          SEQ ID NO:29 tcccgactgacttatcagacactgccacat                          SEQ ID NO:30 atgtggcagtgtctgtcgagtgactcggga                          SEQ ID NO:31 tcccgagtcactagccagacactgccacat                          SEQ ID NO:32

NLTCEVWGPTSPKLMLSLKLENKEAKVSKREKAVWVL                   SEQ ID NO:33
NPEAGMWNCLLSDSGQVLLESNIKVLPTWSTPVQPM

NLTCEVWGPTSPKLMLSLKLENKEAKVSKREKAVWVL                   SEQ ID NO:34
NPEAGMWQCSLSDSGQVLLESNIKVLPTWSTPVQPM

NLTCEVWGPTSPKLMLSLKLENKEAKVSKREKAVWVL                   SEQ ID NO:35
NPEAGMWQCLSSDSGQVLLESNIKVLPTWSTPVQPM

NLTCEVWGPTSPKLMLSLKLENKEAKVSKREKAVWVL                   SEQ ID NO:36
NPEAGMWQCILSDSGQVLLESNIKVLPTWSTPVQPM

NLTCEVWGPTSPKLMLSLKLENKEAKVSKREKAVWVL                   SEQ ID NO:37
NPEAGMWQCLISDSGQVLLESNIKVLPTWSTPVQPM

TSPKLMLSLKLENKEA                                        SEQ ID NO:38

KVSKREKAVWVLNPEA                                        SEQ ID NO:39

DSGQVLLE                                                SEQ ID NO:40

GMWQ                                                    SEQ ID NO:41
``` including homologs, analogs and fragments which maintain IL-16-antagonist activity; wherein
    A=Ala=Alanine
    R=Arg=Arginine
    N=Asn=Asparagine
    D=Asp=Aspartic acid
    B=Asx=Asparagine or aspartic acid
    C=Cys=Cysteine
    Q=Gln=Glutamine
    E=Glu=Glutamic acid
    Z=Glx=Glutamine or Glutamic acid
    G=Gly=Glycine
    H=His=Histidine
    I=Ile=Isoleucine
    L=Leu=Leucine
    K=Lys=Lysine
    F=Phe=Phenylalanine
    P=Pro=Proline
    S=Ser=Serine
    T=Thr=Threonine
    W=Trp=Tryptophan
    Y=Tyr=Tyrosine
    V=Val=Valine
    X=Xaa=Any amino acid Consistent with the observed properties of the peptides of the invention, the present peptides can be used to inhibit, suppress, or cause the cessation of at least one Il-16-mediated biological activity. IL-16 functions in the biochemical events associated with the inflammation reaction in animals as an agonist to induce the migration of CD4$^+$ T-cells. Accordingly, the present invention contemplates methods to block, interrupt or otherwise prevent the association of IL-16 to its receptor on CD4 and thereby effectively treat CD4$^+$-cell associated disorders.

IL-16-mediated disorders such as, for example, asthma, rheumatoid arthritis, inflammatory bowel disease (IBD) and systemic lupus are CD4$^+$-cell dependent and therefore treatable with the IL-16 antagonists, preferably IL-16 antagonist peptides, of the present invention. Other CD4$^+$ cell related diseases are also contemplated by the present invention.

In another embodiment of the present invention, one or more IL-16 antagonists, e.g., IL-16 antagonist peptides or antibodies, are included in pharmaceutical compositions.

Preferably, compositions containing the IL-16 antagonist peptides of the present invention are administered intravenously to inhibit, suppress, or cause the cessation of at least one IL-16-mediated biological activity. When administered intravenously, the peptide compositions may be combined with other ingredients, such as carriers and/or adjuvants. The peptides may also be covalently attached to a protein carrier, such as albumin, so as to minimize clearing of the peptides. There are no limitations on the nature of the other ingredients, except that such ingredients must be pharmaceutically acceptable, efficacious for their intended administration and cannot degrade the activity of the active ingredients of the compositions. Examples of other anti-inflammatory ingredients contemplated by the present invention include, but are not limited to anti-CD4 antibodies, anti-TNFα antibody, NSAIDS, steroids, or cyclosporin-A. When employed together with IL-16 antagonists, these agents may be employed in lesser dosages than when used alone.

The pharmaceutical forms suitable for injection include sterile aqueous solutions or dispersions and sterile powders for the extemporaneous preparation of sterile injectable solutions or dispersions. In all cases the ultimate solution form must be sterile and fluid. Typical carriers include a solvent or dispersion medium containing, for example, water buffered aqueous solutions (i.e., biocompatible buffers), ethanol, polyols such as glycerol, propylene glycol, polyethylene glycol, suitable mixtures thereof, surfactants or vegetable oils. Sterilization can be accomplished by any art-recognized technique, including but not limited to, filtration or addition of antibacterial or antifungal agents, for example, paraben, chlorobutano, phenol, sorbic acid or thimerosal. Further, isotonic agents such as sugars or sodium chloride may be incorporated in the subject compositions.

Production of sterile injectable solutions containing the subject peptides is accomplished by incorporated these compounds in the required amount in the appropriate solvent with various ingredients enumerated above, as required, followed by sterilization, preferably filter sterilization. To obtain a sterile powder, the above solutions are vacuum-dried or freeze-dried as necessary.

When the peptides of the invention are administered orally, the pharmaceutical compositions thereof containing an effective dose of the peptide can also contain an inert diluent, as assimilable edible carrier and the like, be in hard or soft shell gelatin capsules, be compressed into tablets, or may be in an elixir, suspension, syrup or the like.

The subject peptides are thus compounded for convenient and effective administration in pharmaceutically effective amounts with a suitable pharmaceutically acceptable carrier in a therapeutically effective dose.

The peptides should preferably be administered in an amount of at least about 50 mg per dose, more preferably in an amount up to about 500 mg to about 1 gram per dose. Since the peptide compositions of this invention will eventually be cleared from the bloodstream, re-administration of the compositions is indicated and preferred.

The peptides can be administered in a manner compatible with the dosage formulation and in such amount as well be therapeutically effective. Systemic dosages depend on the age, weight and conditions of the patient and on the administration route. For example, a suitable dose for the administration to adult humans ranges from about 0.001 to about 20.0 mg per kilogram of body weight.

As used herein, a pharmaceutically acceptable carrier includes any and all solvents, dispersion media, coatings, antibacterial and antifungal agents, isotonic agents the like. The use of such media and agents are well-known in the art. The pharmaceutically acceptable carriers used in conjunction with the peptides of the present invention vary according to the mode of administration. For example, the compositions may be formulated in any suitable carrier for oral liquid formulation such as suspensions, elixirs and solutions. Compositions for liquid oral dosage include any of the usual pharmaceutical media such as, for example, water, oils, alcohols, flavoring agents, preservatives, coloring agents and the like. In the case of oral solid preparations (capsules and tablets) carriers such as starches, sugars, diluents, granulating agents, lubricants, binders, disintegrating agents and the like may be used. In addition, carriers such as liposomes and microemulsions may be used.

In a further aspect of the present invention, the pharmaceutical compositions of the present invention are employed for the treatment of IL-16 mediated pathological disorders. Thus, the present invention provides methods of treating an IL-16-mediated disorder in a subject by administering a therapeutically effective amount of a pharmaceutical composition of the present invention.

The term "therapeutically effective amount" means the dose required to treat an IL-16 mediated disorder.

By "an IL-16-mediated disorder" is meant a pathological disorder, the onset, progression or the persistence of the symptoms of which requires the participation of IL-16 molecules. Particularly, IL-16-mediated disorders contemplated by the present invention include asthma, rheumatoid arthritis, inflammatory bowel disease, Graves, disease, multiple sclerosis, lupus and bullous pemphigoid.

The term "treatment" or "treat" refers to effective inhibition, suppression or cessation of the IL-16 activity so as to prevent or delay the onset, retard the progression or ameliorate the symptoms of the disorder.

The term "subject" refers to any mammalian subject. Preferably, the subject is a human.

The present invention thus provides methods of interfering with, blocking or otherwise preventing the interaction or binding of IL-16 with an IL-16 receptor by employing the IL-16 antagonists contemplated by the present invention.

The IL-16 antagonist peptides of the present invention (or homologs, analogs or fragments) can be used to raise single-chain antibodies (SAb) or humanized monoclonal antibodies useful in the invention. The peptides can be coupled to a carrier protein such as KLH as described in Ausubel et al. (1989) Current Protocols in Molecular Biology, John Wiley & Sons, New York. The KLH-antagonist peptide is mixed with Freund's adjuvant and injected into guinea pigs, rats, donkeys and the like or preferably into rabbits. Antibodies may be purified by peptide antigen affinity chromatography.

A single-chain antibody (SAb) is created by fusing together the variable domains of the heavy and light chains using a short peptide linker, thereby reconstituting an antigen binding site on a single molecule. Such single-chain antibody variable fragments (Fvs) can be fused to all or a portion of the constant domains of the heavy chain of an immunoglobulin molecule, if necessary. The use of sAb avoids the technical difficulties in the introduction of more than one gene construct into host cells. Single chain antibodies and methods for their production are known in the art. See, e.g., Bedzyk et al. (1990) *J. Biol. Chem.,* 265:18615; Chaudhary et al. (1990) *Proc. Natl. Acad. Sci.,* 87:9491; U.S. Pat. No. 4,946,778 to Ladner et al.; and U.S. Pat. No. 5,359,046 to Capon et al.

Monoclonal antibodies can be prepared using IL-16 antagonist peptides and standard hybridoma technology (see e.g. Kohler et al., (1975) Nature 256:495; Hammerling et al., (1981) In Monoclonal Antibodies and T Cell Hybridomas, Elsevier, N.Y.). For example, monoclonal antibodies to IL-16 antagonist peptides (homologs, analogs or fragments thereof) can be raised in Balb/C or other similar strains of mice by immunization with purified or partially purified preparations of IL-16 antagonist peptides. The spleens of the mice can be removed, and their lymphocytes fused to a mouse myeloma cell line. After screening of hybrids by known techniques, a stable hybrid will be isolated that produces antibodies against IL-16 antagonist peptides. Such activity can be demonstrated by the ability of the antibody to prevent the binding of radiolabelled IL-16 to the CD4 receptor. The monoclonal antibody can then be examined for its ability to inhibit the biological activity of IL-16, e.g. cell migration. Once produced, monoclonal antibodies are tested for specific IL-16 recognition by Western blot or immunoprecipitation analysis (by methods described in Ausubel et al., supra). Antibodies which antagonize IL-16/CD4 receptor binding or IL-16 mediated CD4 receptor function are considered to be useful antagonists in the invention.

The monoclonal antibodies of the present invention can be humanized to reduce the immunogenicity for use in humans. One approach is to make mouse-human chimeric antibodies having the original variable region of the murine mAb, joined to constant regions of a human immunoglobulin. Chimeric antibodies and methods for their production are known in the art. See, e.g., Cabilly et al., European Patent Application 125023 (published Nov. 14, 1984); Taniguchi et al., European patent Application 171496 (published Feb. 19, 1985); Morrison et al., European Patent Application 173494 (published Mar. 5, 1986); Neuberger et al., PCT Application WO 86/01533, (published Mar. 13, 1986); Kudo et al., European Patent Application 184187 (published Jun. 11, 1986); Robinson et al., International Patent Publication #PCT/US86/02269 (published May 7, 1987); Liu et al., *Proc. Natl. Acad. Sci. USA* 84:3439–3443 (1987); Sun et al., *Proc. Natl. Acad. Sci. USA* 84:214–218 (1987); Better et al., *Science* 240:1041–1043 (1988). These references are incorporated herein by reference. Generally, DNA segments encoding the H and L chain antigen-binding regions of the murine mAb can be cloned from the mAb-producing hybridoma cells, which can then be joined to DNA segments encoding $C_H$ and $C_L$ regions of a human immunoglobulin, respectively, to produce murine-human chimeric immunoglobulin-encoding genes.

The invention is further illustrated by the following specific examples which are not intended in any way to limit the scope of the invention.

EXAMPLE 1

Cell migration was assessed using a modified Boyden chamber. (Center, et al., (1982) *J. Immunol.* 128:2563–2568; Cruikshank, et al., (1982) *J. Immunol.* 128:2569–2574). Murine splenocytes ($5 \times 10^6$ cells/ml) in M199-HPS (or M199-HPS alone) was added to the bottom wells. For blocking experiments, $10^{-9}$ M murine rIL-16 with various concentrations of oligopeptides were mixed and placed in the lower well. The upper and lower wells were separated by 8 μm pore size nitrocellulose filter membrane (Neuro Probe). Following incubation (3 h, 37° C.), the membranes were removed, stained with hematoxylin, and dehydrated. Cell migration was quantified by counting the number of cells migrating beyond a depth of 40 μm. Counts were compared with control cells exposed to M199-HPS alone, which was normalized to 100%. Cell migration is expressed as the mean % control migration. All samples were tested in duplicate, with five high power fields counted in each duplicate.

Results from multiple experiments were analyzed using Student's t test for paired variables, and Tukey's test for multiple variables. A P value<0.05 was considered significant.

Synthetic oligopeptides based on murine D4 domain sequences with the highest homology to human CD4 (FIG. 2) were prepared and tested for their ability to block murine rIL-16-stimulated murine splenocyte migration. Three 12-residue D4-based oligopeptides designated A (SEQ ID NO:15), B (SEQ ID NO:14), and C (GDKVKMDSRIQV; SEQ ID NO:19) had IL-16-inhibitory activity. Peptide B (aa 341–352) includes the sequence WQCLLS (residues 344–349, SEQ ID NO:4) which is 100% conserved in all the species examined. Peptide A (aa 327–338) and peptide C (aa 351–362) correspond to the N-terminal and C-terminal flanks of peptide B, respectively. A random scrambled 12-residue peptide (LSKQKMVSREGT) designated peptide D (SEQ ID NO:20) was used a negative control for non-specific effects of peptide administration on splenocyte motility. Criteria for the design of peptide D included overall hydrophilicity, neutral charge and no cysteine residues (to prevent possible dimer formation).

EXAMPLE 2

The predicted amino acid sequences of the four extracellular immunoglobulin-like domains of CD4 from different species were compared by the method of Lipman and Pearson (supra), using Lasergene software (DNASTAR). Each of these four domains (designated D1 through D4) of cat (Norimine et al (1992) *Immunol.* 75:74–79), dog (Gorman et al. (1994) *Tissue Antigens* 43:184–188), rabbit (Hague et al. (1992) *Proc. Natl. Acad. Sci. U.S.A.* 89:7963–7967), rat (Clark et al. (1987) *Proc. Natl. Acad. Sci. U.S.A.* 84:1649–1653), and mouse (Littman et al. (1987) *Nature* 453–455) were compared with the predicted human (Maddon et al. (1985) *Cell* 42:93–104) CD4 sequence (FIG. 1). In each case, the D4 domains were found to have a higher similarity index than the other three domains.

Four 6-amino acid peptides were synthesized based on the native murine CD4 D4 domain sequence: VSEEQK (aa 327–338. SEQ ID NO:18); VVQVVA (aa 333–338, SEQ ID NO:9); WQCLLS (aa 344–349, SEQ ID NO:4); and VAPETG (aa 337–342, SEQ ID NO:21). Five 6-amino acid peptides were derived based on the above peptides but with selected non-conservative amino acid substitutions: VKQVVA (aa 334 V:K, SEQ ID NO:10); VVQKVA (aa 336 V:K, SEQ ID NO:11); WACLLS (aa 345 Q:A, SEQ ID NO:6); WQALLS (aa 346 C:A, SEQ ID NO:5); WQCELS (aa 347 L:E, SEQ ID NO:7).

Murine spleens were harvested from healthy 8-week male BALB/c mice (Jackson Laboratory). Splenocytes were isolated by grinding spleens between frosted slides in M199 culture medium (M.A. Bioproducts), supplemented with 0.4% bovine serum albumin, 22 mM HEPES buffer, 100 with U/ml of penicillin, 100 μg/ml streptomycin (M199-HPS). Cells were washed and erythrocytes were lysed in Gey's solution. Splenocytes were washed twice in M199, and resuspended to a final concentration of $2 \times 10^6$ cells/ml in RPMI1640 medium (BioWhittaker) supplemented with 10% FBS, 100 U/ml of penicillin and 100 μg/ml of streptomycin. By flow cytometry, 25% of the isolated splenocytes within the lymphocyte-cloud were $CD4^+$.

Recombinant murine IL-16 was produced in *Escherichia coli* (strain HMS 174; Novagen) as a polyhistidine fusion protein containing the 119 C-terminal residues encoded by the previously reported murine cDNA (Keane et al., (1998) *J. Immunol.* 160: 5945–5954), using the bacterial expression vector pET16b (Novagen). The recombinant product corresponds to the secreted form of natural murine IL-16 following cleavage by caspase-3 (Zhang et al. (1998) *J. Biol. Chem.* 273:1144–1149). The rIL-16 was purified by metal chelation chromatography, and the polyhistidine tag was cleaved with factor Xa (New England Biolabs).

EXAMPLE 3

Induction of IL-2R (CD25) on rIL-16-stimulated murine splenocytes was detected by staining with FITC-conjugated anti-mouse IL-2R Ab (PharMingen). Cells were fixed with 10% formalin and stored at 4° C. in the dark before analysis with a Becton Dickinson FACScan 440 flow cytometer. The % $IL-2R^+$ cells was determined by subtracting the % isotype control positive from the total % positive events.

To demonstrate that peptide inhibition was not limited to the chemoattractant activity of IL-16, the D4 sequence peptides were tested for their capacity to inhibit IL-16-stimulated induction of IL-2R on resting murine splenocytes prepared in accordance with Example 1. As shown in Table 1, rIL-16 increased basal IL-2R expression by 50% and this was completely inhibited by peptide B (SEQ ID NO:14) at $10^{-6}$ M and $10^{-7}$M. Peptides A (SEQ ID NO:15) and C (SEQ ID NO:19) were inhibitory at $10^{-7}$ M, but not $10^{-6}$ M. The negative control peptide D (SEQ ID NO:20) ($10^{-6}$ M) had no effect on rIL-16-stimulated IL-2R expression. The D4 region peptides were equally potent inhibitors of two distinct IL-16 bioactivities, the induction of motility and the upregulation of IL-2R.

TABLE 1

| CD4 Peptides Inhibit IL-2R Induction by rIL-16 | |
|---|---|
| CONDITION | % $IL-2R^+$ CELLS |
| No stimulation | 24 |
| rIL-16 $10^{-9}$ M | 36 |
| IL-16 + peptide A: | 21 |
| IL-16 + peptide A: | 37 |
| IL-16 + peptide B: | 22 |
| IL-16 + peptide B: | 26 |
| IL-16 + peptide C: | 20 |
| IL-16 + peptide C: | 35 |
| IL-16 + peptide D: | 37 |

Murine splenocytes were incubated in control buffer, rIL-16 alone, or rIL-16 plus the indicated peptide. IL-2R expression was determined by flow cytometry using FITC-conjugated anti-IL-2R antibody. The % $IL-2R^+$ was determined by subtracting the FITC-conjugated isotype control antibody binding from the FITC-conjugated anti-IL-2R antibody binding. Isotype control antibody binding ranged from 1% to 4%.

Figure 3:
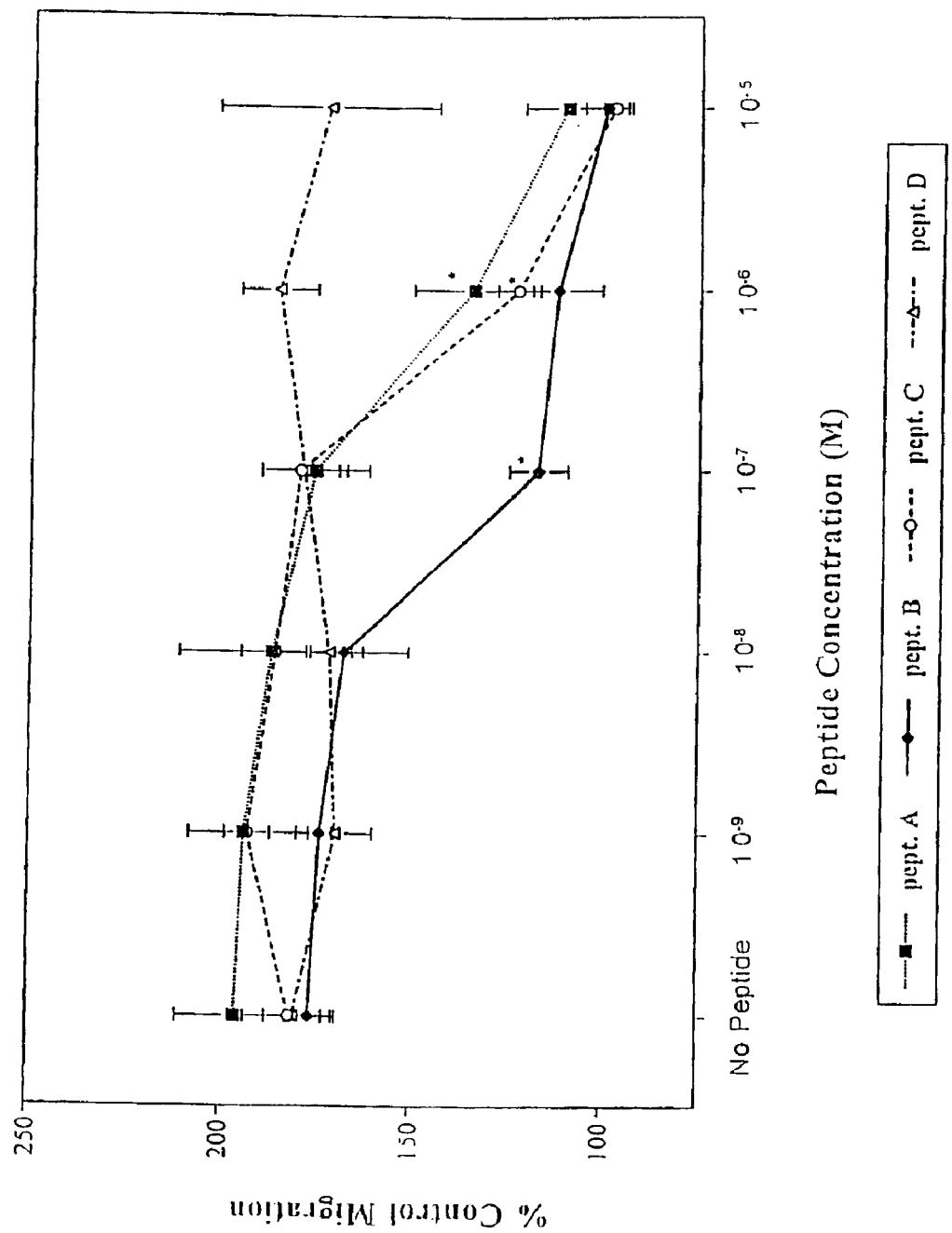
FIG. 3 Demonstrates IL-16 inhibition by 12-residue domain 4 peptides. The 12-residue peptides A, B, and C were tested for their capacity to inhibit murine IL-16 induced murine splenocyte chemotaxis. Serial $\log_{10}$ dilutions of each peptide from $10^{-5}$ M to $10^{-9}$ M, or control buffer without peptides, were combined with rIL-16 ($10^{-9}$ M) and applied to the lower wells of Boyden microchemotaxis chambers. Peptide D is a random 12-residue oligopeptide used as a negative control. Cell migration was compared with migration in control buffer without IL-16 or peptides. Results are expressed as the mean % unstimulated control migration±SEM for five experiments. Asterisks indicate a significant difference ($p<0.05$) in migration between cells stimulated with rIL-16 alone and cells stimulated with rIL-16 in the presence of peptide.
Figure 5:
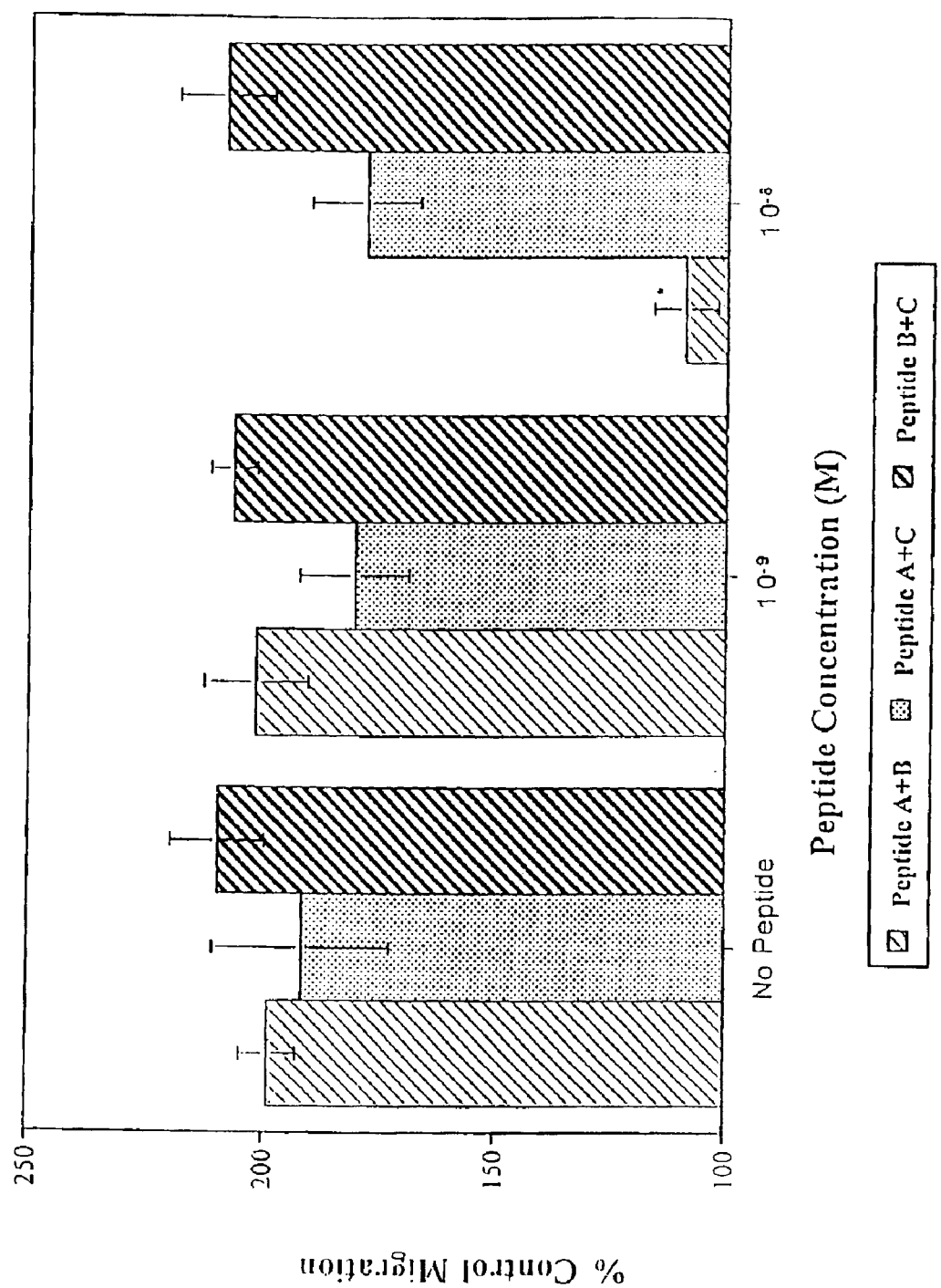
FIG. 5 Demonstrates synergistic inhibition of IL-16 by peptide A and peptide B. The cooperative effects between the three 12-residue IL-16-inhibiting peptides was tested using paired combinations of each peptide at suboptimal final concentrations of $10^{-8}$ M and $10^{-9}$ M. The capacity of these combined peptides to inhibit the chemoattractant activity of rIL-16 ($10^{-9}$) was tested. Results are expressed as the mean % control migration±SEM for four experiments. Asterisks indicate a significant difference ($p<0.05$) in migration between cells stimulated with rIL-16 alone and cells stimulated with rIL-16 in the presence of peptide.

Peptides A (SEQ ID NO:15) and C (SEQ ID NO:19) inhibited rIL-16-induced splenocyte migration at $10^{-6}$ M. The corresponding regions in the D4 domain of CD4 were assayed to assess their involvement in cell activation by IL-16. It was believed that a combination of IL-16-inhibiting peptides would be synergistic if they simultaneously blocked IL-16 binding at distinct touch points on CD4, or if contact with discrete binding and activating domains was blocked. This was investigated using combinations of peptides A (SEQ ID NO: 18), B (SEQ ID NO:14), and C (SEQ ID NO:19) at sub-optimal inhibitory concentrations. As shown in FIG. 3, none of the three peptides alone at $10^{-8}$ M inhibited IL-16 activity. However, the combination of peptide A and peptide B at a final concentration $10^{-8}$ M significantly inhibited chemotaxis (FIG. 5). The combination of peptide A plus peptide C, or peptide B plus peptide C, did not inhibit IL-16 at this concentration. These data suggested that sequences within both peptide A and peptide B were important for IL-16 activation via CD4. The failure of VAPETG (SEQ ID NO:21) to block IL-16 favored a model with discrete touch points.

These results indicated that certain D4 domain peptides specifically inhibit IL-16-stimulated splenocyte motility.

EXAMPLE 4

Figure 4:
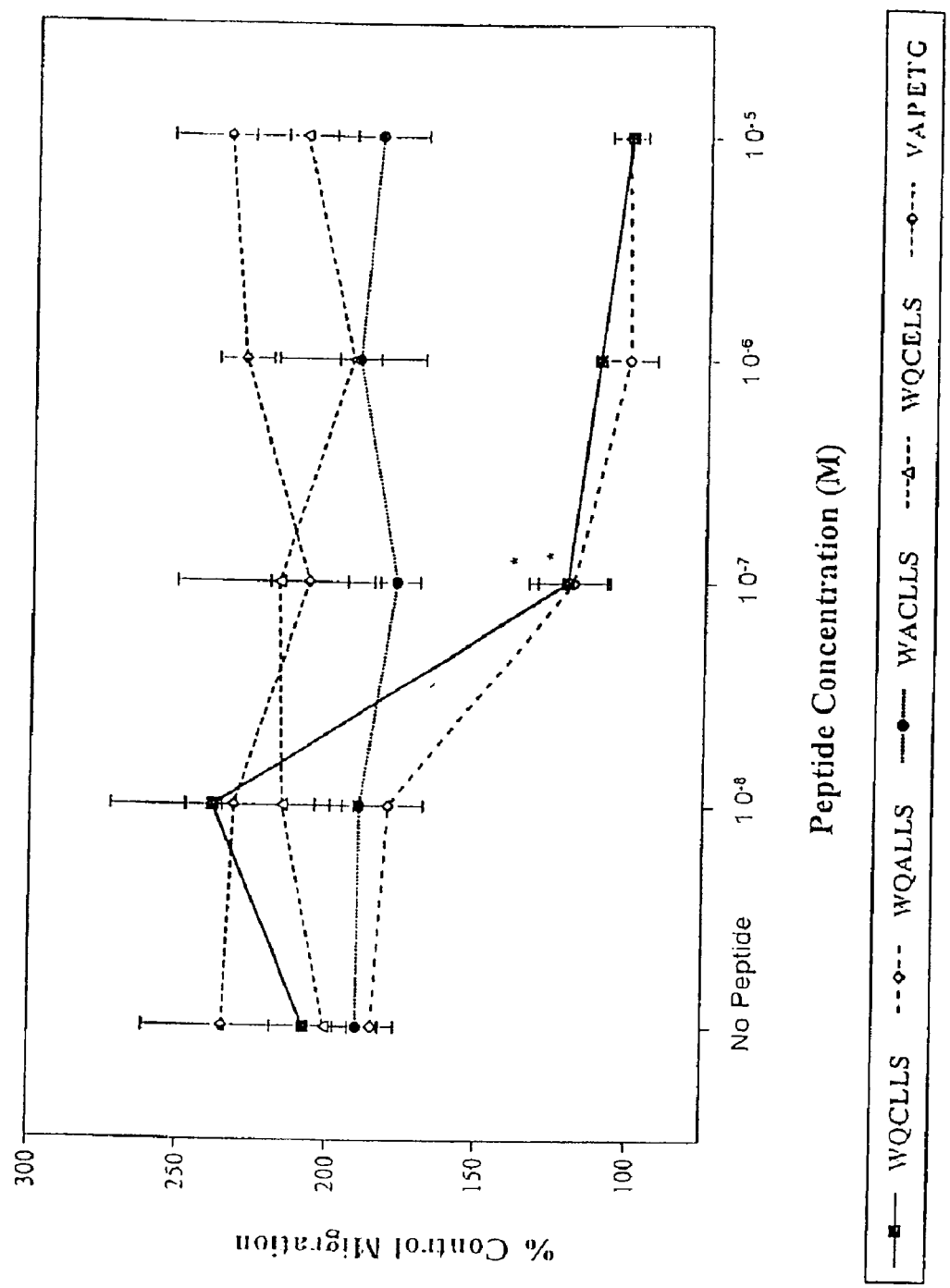
FIG. 4 Provides identification of critical residues within peptide B (SEQ ID NO:14). The inhibitory activity of the 6-residue core WQCLLS (SEQ ID NO:4) was tested, along with the peptides WQALLS (SEQ ID NO:5), WACLLS (SEQ ID NO:6), and WQCELS (SEQ ID NO:7) each of which has a non-conservative amino acid substitution compared with the native sequence. The peptide VAPETG represents native D4 sequences bridging peptides A and B. The effect of these peptides on murine splenocyte migration in response to $10^{-9}$ M rIL-16 was tested. Results are expressed as the mean % control migration±SEM for three experiments. Asterisks indicate a significant difference ($p<0.05$) in migration between cells stimulated with rIL-16 alone and cells stimulated with rIL-16 in the presence of peptide.

Within peptide B, the six residues WQCLLS (SEQ ID NO:4) are highly conserved between species. Human and murine peptide B share 100% homology with respect to residues WQCLLS. A synthetic WQCLLS was prepared by solid phase peptide synthesis. The WQCLLS (SEQ ID NO:4) oligopeptide inhibited IL-16 at $10^{-7}$ M (FIG. 4), comparable to the activity of the 12-residue peptide B (SEQ ID NO:14). Mutagenesis experiments with truncated peptide B indicated that the $Trp^{344}$ and $Ser^{349}$ residues are dispensable with respect to IL-16 inhibition (data not shown). The substituted peptide WQALLS (SEQ ID NO:5) was equally as effective as the native WQCLLS (SEQ ID NO:4), suggesting that $Cys^{346}$ is also dispensable. In contrast, the substituted peptides WACLLS (SEQ ID NO:6) and WQCELS (SEQ ID NO:7) failed to block IL-16. The peptide VAPETG (SEQ ID NO:21) which bridges sequences between peptide A and peptide B lacked inhibitory activity, indicating that the two C-terminal residues of peptide A, the two intervening residues between peptides A and B, and the two N-terminal residues of peptide B were dispensable.

Figure 6:
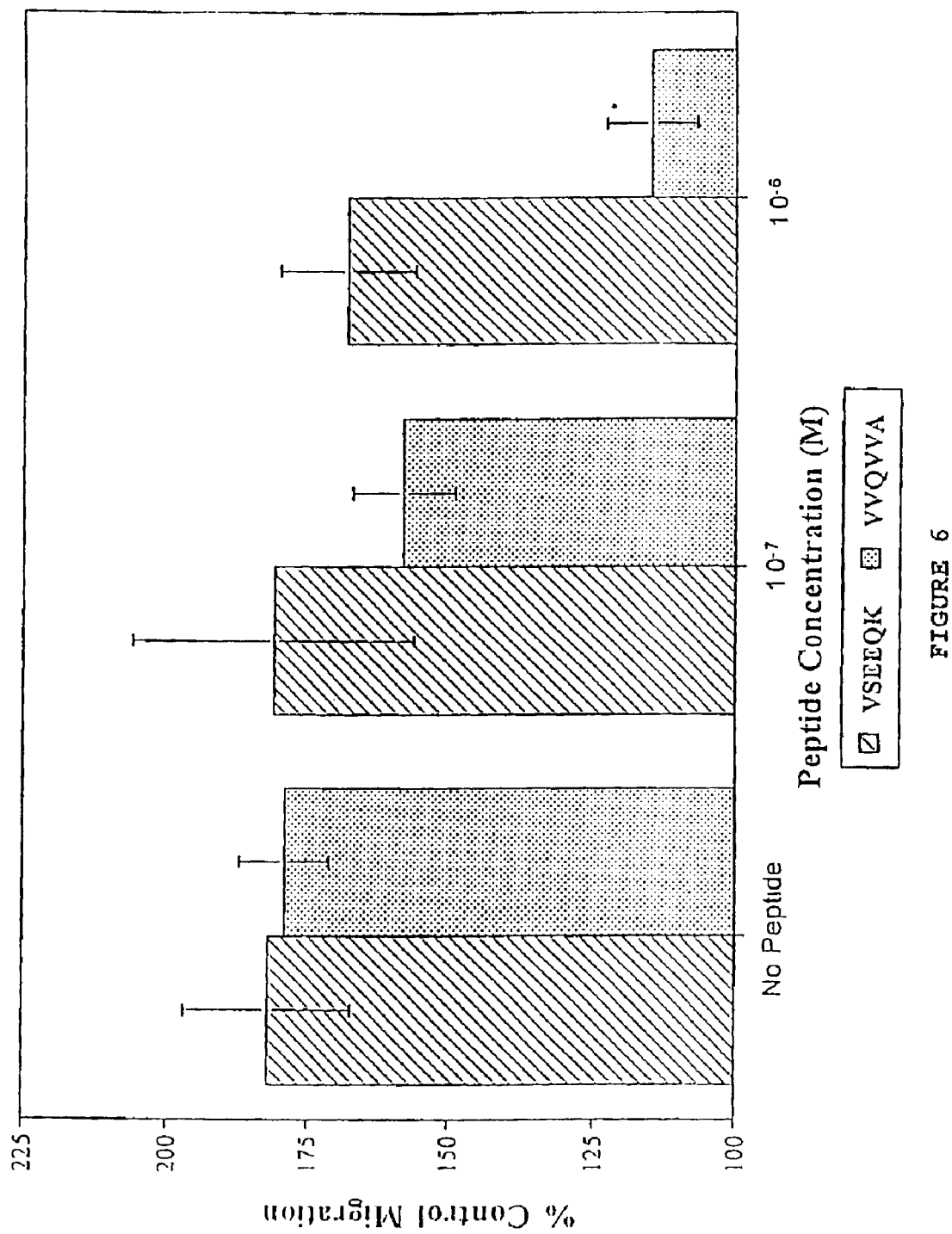
FIG. 6 Provides identification of residues in peptide A required for IL-16 inhibition. The 6-residue peptides VSEEQK (SEQ ID NO:18) and VVQVVA (SEQ ID NO:9) represent the N-terminal and C-terminal halves of peptide A (SEQ ID NO:15), respectively. Each was tested for IL-16 inhibition in the Boyden chamber chemotaxis assay. Results are expressed as the mean % control migration±SEM. The data for VSEEQK represents five experiments and the data for VVQVVA represents four experiments. The asterisk indicates a significant difference ($p<0.05$) in migration between cells stimulated with rIL-16 alone and cells stimulated with rIL-16 in the presence of peptide.

To identify the residues that were responsible for the synergistic effect of peptide A, two 6-residue peptides were prepared in accordance with Example 1: VSEEQK (SEQ ID NO:18) and VVQVVA (SEQ ID NO:9) represent the N-terminal half and the C-terminal half of peptide A, respectively. The C-terminal half-sequence VVQVVA (SEQ ID NO:9) inhibited rIL16-induced splenocyte migration at $10^{-6}$ M comparably to peptide A, while the N-terminal VSEEQK (SEQ ID NO:18) demonstrated no inhibitory activity (FIG. 6). Furthermore, VVQVVA at $10^{-8}$ M had synergistic activity with peptide B, while no synergy was observed when peptide B was combined with VSEEQK (data not shown).

Figure 7:
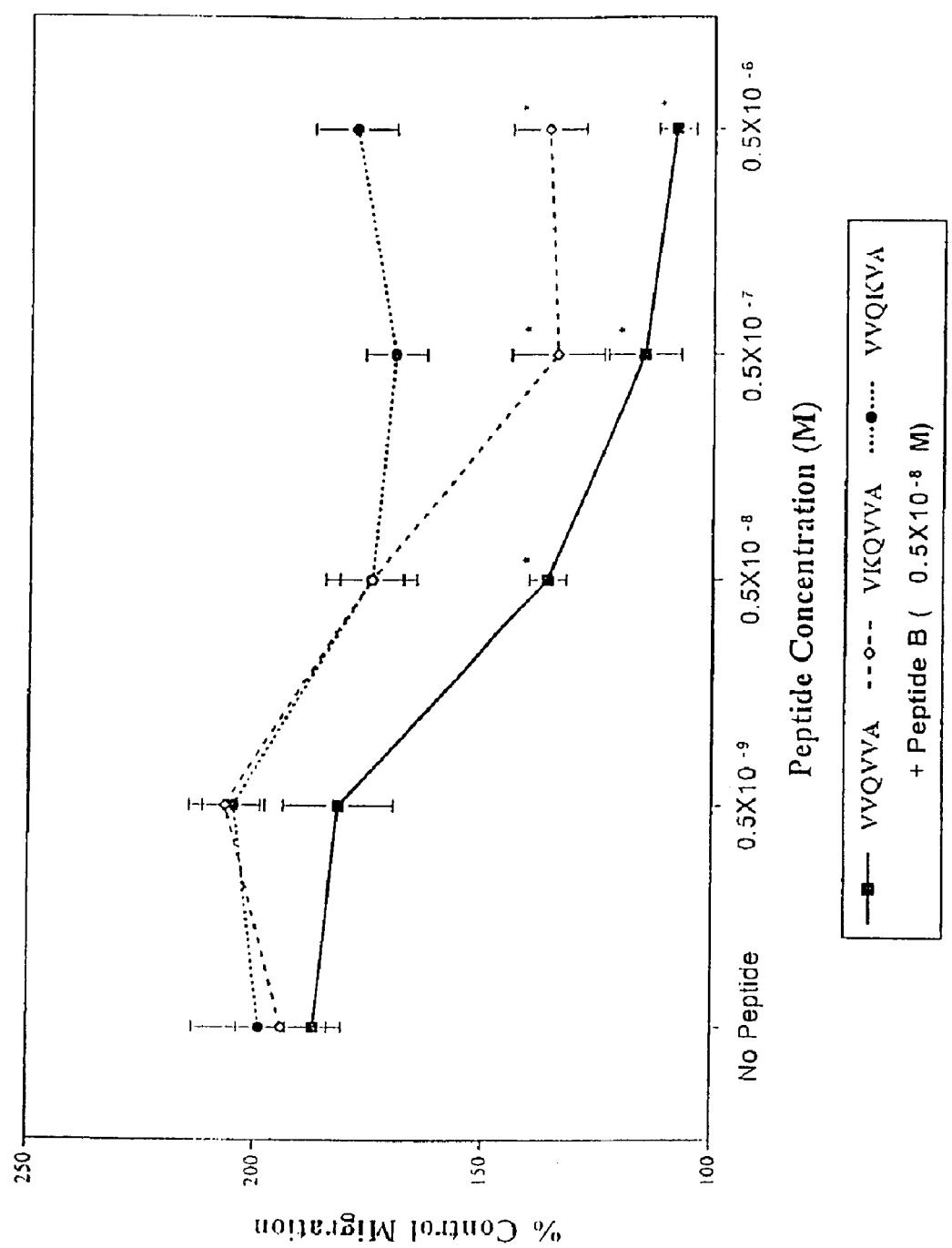
FIG. 7 Provides identification of residues in VVQVVA (SEQ ID NO:9) required for IL-16 inhibition. The native sequence peptide VVQVVA and two related oligopeptides with non-conservative amino acid substitutions (VKQVVA (SEQ ID NO:10) and VVQKVA (SEQ ID NO:11)) were evaluated for their capacity to act synergistically with peptide B in blocking IL-16-stimulated splenocyte motility. Each of the indicated 6-residue peptides at the concentrations indicated in the figure ($0.5\times10^{-6}$ M to $0.5\times10^{-9}$ M) were combined with peptide B at a fixed concentration of $0.5\times10^{-8}$ M. Results are expressed as the mean % control migration±SEM for three experiments. Asterisks indicate a significant difference ($p<0.05$) in migration between cells stimulated with rIL-16 alone and cells stimulated with rIL-16 in the presence of peptide.

To identify residues in VVQVVA required for IL-16 inhibition, and for synergy with peptide B, non-conservative substitutions were tested. Sequence comparison across species showed that $Val^{334}$ and $Val^{336}$ were conserved in all cases studied except that for rat whose sequence is VIQVQA (SEQ ID NO:22). The substituted oligopeptides VKQVVA (SEQ ID NO:10) and VVQKVA (SEQ ID NO:11) were compared with the native sequence peptide VVQVVA (SEQ ID NO:9) for inhibition of IL-16-stimulated splenocyte motility. Each peptide was separately combined at various concentrations ($0.5 \times 10^{-6}$ M to $0.5 \times 10^{-9}$ M) with a sub-optimal concentration of peptide B (fixed at a constant $0.5 \times 10^{-8}$ M). As shown in FIG. 7, the substituted peptide VVQKVA (SEQ ID NO:11) plus peptide B (SEQ ID NO:14) did not block IL-16 at any concentration, while the substituted peptide VKQVVA (SEQ ID NO:10) in combination with peptide B (SEQ ID NO:14) reduced IL-16-stimulated splenocyte migration at $10^{-6}$ and $10^{-7}$ M. These data provided evidence that the D4 region residues $Val^{334}$ and $Val^{336}$ were critical for IL-16 stimulation via CD4.

EXAMPLE 5

Radiolabeled murine IL-16 was prepared by in vitro translation and transcription (TNT T7, Promega) of a murine IL-16 CDNA construct in pET-16b expressing the C-terminal 119 amino acids of IL-16. Each coupled transcription-translation reaction was conducted in medium supplemented with [$^{35}$S] methionine according to the manufacturer's instructions.

A glutathione-S-transferase (GST)-murine D3D4 fusion protein was produced by subcloning the murine D3D4 domain cDNA sequences encoding the CD4 protein open reading frame from $Phe^{182}$ to $Phe^{372}$ into pGEX-5X.1 (Pharmacia). The GST-D3D4 fusion protein was purified according to the Pharmacia GST-fusion protein purification protocol using glutathione-conjugated Sepharose 4B beads in the presence of 2 mM dTT. Native GST was purified using the same method, for use as a control in the in vitro binding experiments.

To investigate IL-16 interaction with the D3D4 of CD4, the GST-D3D4 fusion protein, or GST alone, was bound to the glutathione-conjugated Sepharose 4B beads. Five µl of the in vitro translation product containing $^{35}$S-labeled rIL16 was added to 15 µl of the bead-bound proteins in 230 µl of PBS and 50 µl of NETN buffer (150 mM NaCl, 1 mM EDTA, 0.5% NP 40, and 50 mM Tris, pH 8.0). After incubating at 4° C. for 2 h, the beads were washed 3 times in NETN buffer. The GST-D3D4 or GST proteins were released from the beads by boiling in SDS gel loading buffer, and the supernatant was analyzed by 12% SDS-polyacrylamide gel electrophoresis (SDS-PAGE). The presence of $^{35}$S-labeled mrIL16 was detected by autoradiography of the dried gel. Specificity was demonstrated by competition with an excess ($10^{-5}$ M) of unlabeled rIL-16, and the effects of the three 12-residue D3D4 domain peptides on rIL-16 binding was tested by adding each peptide ($10^{-5}$ M) to the binding reaction at time zero.

The ability of D4 oligopeptide sequences to block the chemoattractant activity of IL-16 was mediated by structural mimicry of binding sites for IL-16 on its receptor.

Figure 8:
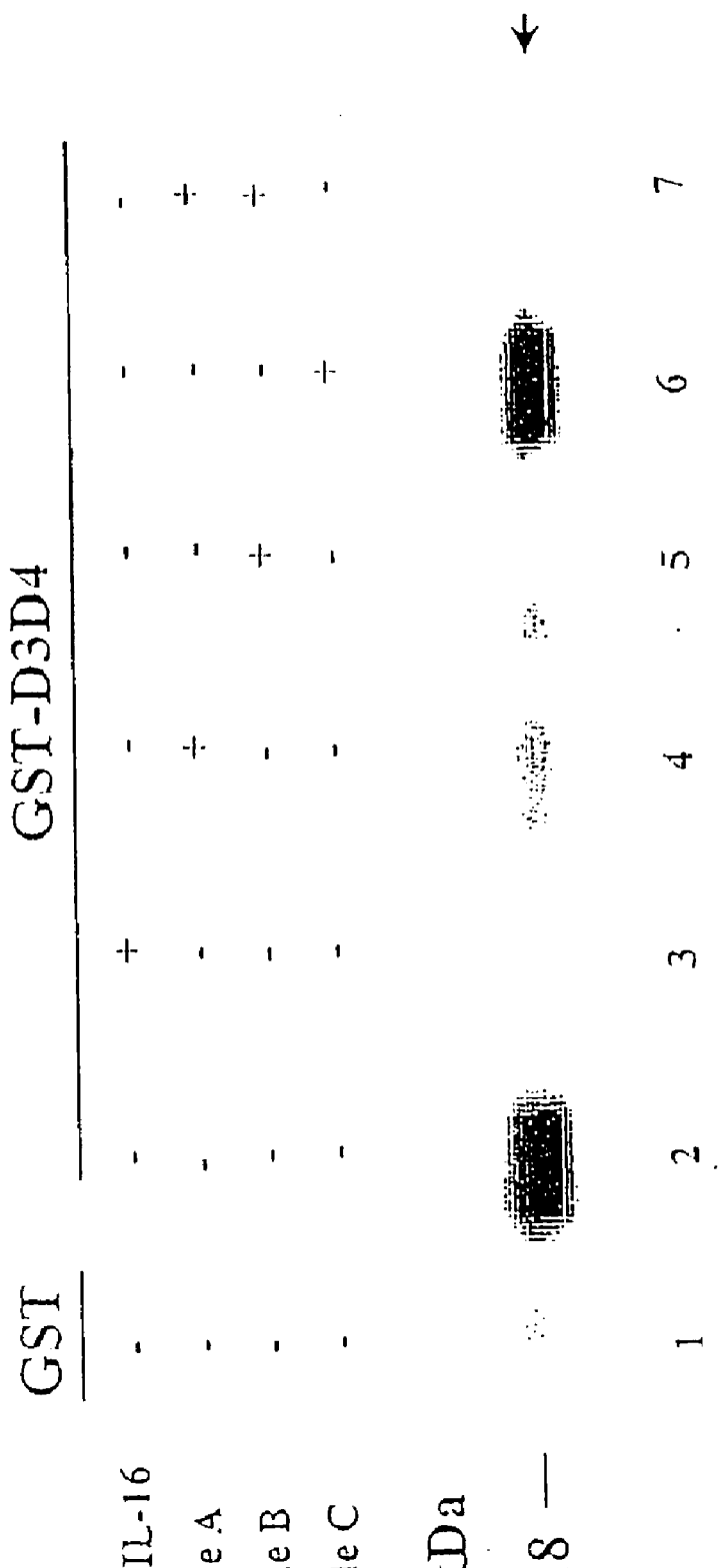
FIG. 8 Demonstrates inhibition of IL-16 binding to D3D4 in vitro. $^{35}$S-labeled murine rIL-16 was incubated with recombinant GST-murine D3D4 fusion protein (rGST-D3D4) or native rGST, attached to glutathione-conjugated Sepharose 4B beads. Complexes were isolated by centrifugation, then bound rIL-16 was released by boiling in SDS-PAGE buffer, resolved by SDS-PAGE, and detected by autoradiography. Specificity of the interaction between rIL-16 and D3D4 was assessed by competition with an excess of unlabeled rIL-16. $^{35}$S-labeled rIL-16 incubated with GST (lane 1); $^{35}$S-labeled rIL-16 incubated with GST-D3D4 (lane 2); $^{35}$S-labeled rIL-16 plus excess unlabelled rIL-16 incubated with GST-D3D4 (lane 3); $^{35}$S-labeled rIL-16 plus 10 ug/ml peptide A (lane 4); $^{35}$S-labeled rIL-16 plus 10 ug/ml peptide B (lane 5); $^{35}$S-labeled rIL-16 plus 10 ug/ml peptide C (lane 6); ); $^{35}$S-labeled rIL-16 plus 10 ug/ml peptide A and peptide B (lane 7). The arrow indicates the position of IL-16 on the gel. The identity of this band was re-confirmed by immunoblotting with anti-IL-16 antibody.

To confirm that IL-16 interacts directly with CD4, an in vitro binding system was developed. A recombinant chimeric protein consisting of GST fused to the N-terminus of the murine CD4 D3D4 region was expressed in E. coli as detailed in Example 1. Radiolabeled murine rIL-16 produced by in vitro transcription and translation in the presence of [$^{35}$S] methionine was incubated with GST-D3D4 bound to glutathione-conjugated Sepharose 4B beads. Native GST was also tested for each condition to control for non-specific binding. Following incubation of $^{35}$S-labeled rIL-16 with GST-D3D4 or GST coated beads, complexes were washed three times then boiled in SDS-PAGE sample buffer prior to electrophoresis and autoradiography. Although some background binding of rIL-16 to native GST was observed, binding to GST-D3D4 was much more intense and was specifically competed by an excess of unlabelled rIL-16 (FIG. 8).

IL-16 binding in this system was reduced to background in the presence of either peptide A (SEQ ID NO:15) or peptide B (SEQ ID NO:14) alone, and with peptide A and B combined. In contrast, peptide C (SEQ ID NO:19) failed to reduce IL-16 binding. These data indicate that peptide A and peptide B function as sequestering receptor antagonists for IL-16. The ability of peptide C to inhibit IL-16-stimulated splenocyte motility at $10^{-6}$ M was mediated by a different mechanism.

EXAMPLE 6

The crystal structure of the D3 and D4 domains of rat CD4 (Brookhaven Protein Data Bank ID 1cid.pdb) were chosen to model domain 4 of murine CD4 that contained the oligopeptide sequences VSEEQKVVQVVA (SEQ ID NO:15) TGLWQCLLSEGD (SEQ ID NO:14), and GDKVKMDSRIQV (SEQ ID NO:19). The program "O" (Jones et al. (1991) Acta Crystallographica—Section a—Foundations of Crystallography 47:110–119) was used to determine secondary structure. The program MOLMOL (Koradi et al. (1929) J. Mol. Graphics 14:51–55) was used to create ribbon diagrams and solvent accessible surface maps.

The locations of the three 12-residue oligopeptide sequences, and of those amino acids critical for IL-16 inhibition, were evaluated in the context of the 3-dimensional structure of rat CD4 and previous studies demonstrating CD4—CD4 dimer formation (reviewed in (Song et al., (1998) Immunol. Today 19:455–461)). The sequence homology between rat and mouse CD4 domains 3 and 4 was 87%. The tertiary structure of murine CD4 was similar to the rat CD4. The sequences of the 12-residue murine peptides used the experiments were conserved in relationship to the corresponding sequences of rat CD4, with the exception of Val$^{337}$ which is Gln in rat. This residue was located in a beta strand and was solvent-exposed in the rat structure, which provided evidence that this amino acid difference would not affect the core packing of domain 4, thus preserving the tertiary structure.

Figure 9A:
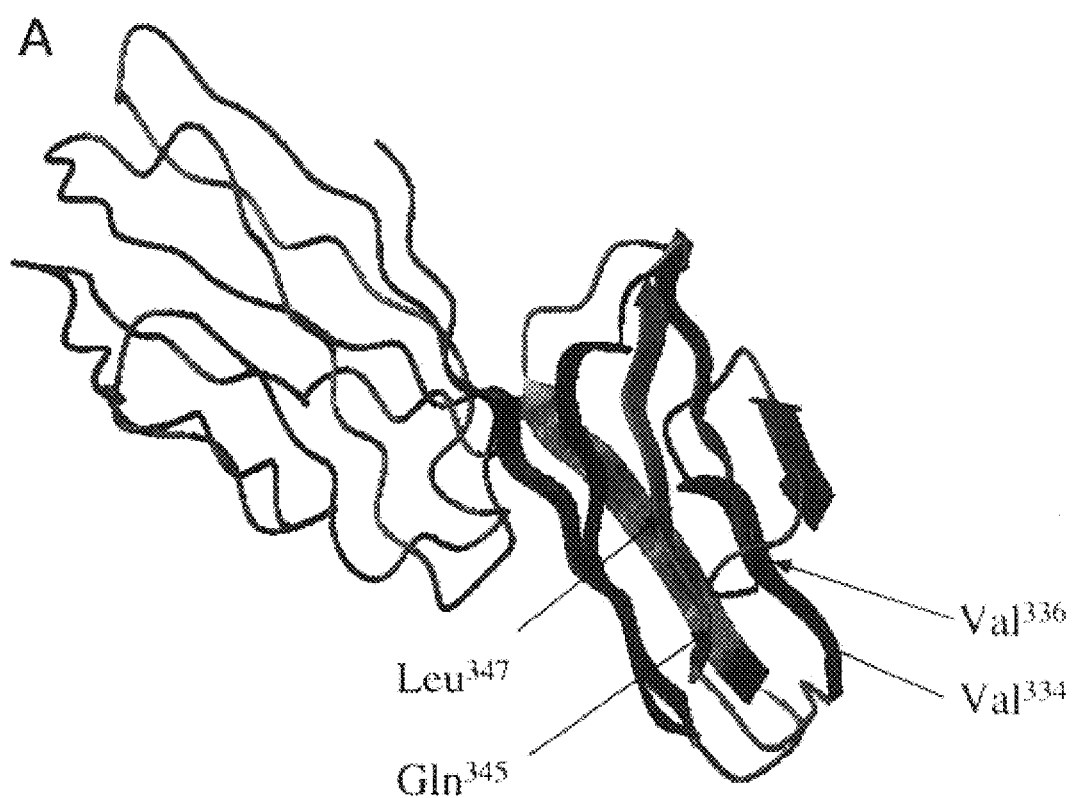
FIG. 9A Illustrates structural modeling of domains 3 and 4 of rat CD4, using the programs "O" and MOLMOL (Jones, et al. (1991) Acta Crystallographica—Section a—Foundations of Crystallography 47:110–119). A, Ribbon diagram of domains 3 and 4 of rat CD4. Beta sheets are depicted as flat ribbons on D4 only. Location of residues comprising peptide A (blue), peptide B (red), peptide C (green) are indicated by arrows, along with the residues lying between peptides A and B (gold), and the residues overlapping between peptides B and C (red-orange).

A ribbon diagram of domains 3 and 4 of rat CD4 was generated (FIG. 9A). Beta sheets were depicted as flat ribbons on domain 4 only. The sequence corresponding to peptide A (colored blue in the figure) was located in strands C', E, and the EF loop. Peptide B (colored red) spanned the C-terminal half of the EF loop, all of the F strand, and a portion of the FG loop. Peptide C (colored green) corresponded to the FG loop and G strand. The residues lying between peptide A and B were colored gold, while those shared by peptides B and C were in orange. The two faces of the beta sandwich formed an apex at the EF loop. Residues in peptides A and B which are proximal to the EF loop constituted a binding site, as can be seen in FIG. 9A. The modeling results indicated that peptide A does not lie within the predicted dimerization region of domain 4 (Wu et al., Nature 387:527–530). However, portions of peptide B were found within the dimer interface, particularly Gln$^{345}$ (corresponding to Gln$^{346}$ in human CD4) that is in the center of the interface zone. Peptide C also partially overlapped the suggested dimerization region of D4.

Figure 9B:
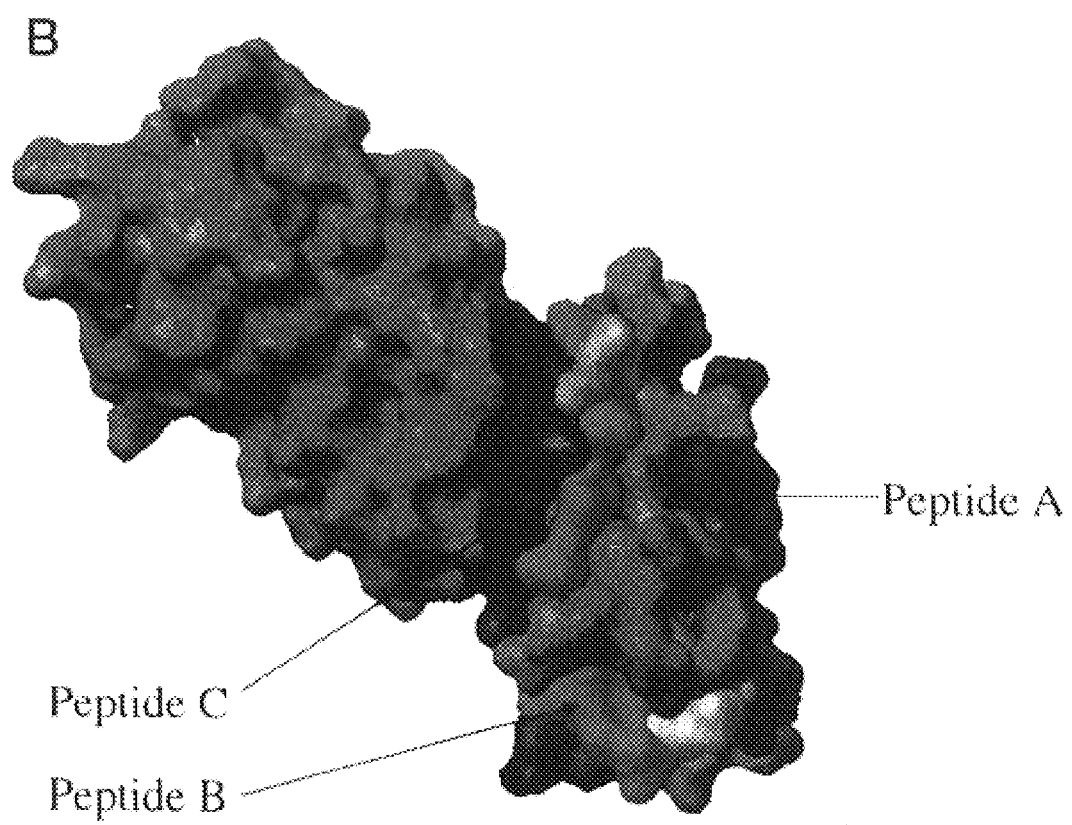
FIG. 9B Illustrates a solvent-accessible surface map of D4. Residues corresponding to peptides A are colored blue, peptide B in red, and peptide C in green.

A solvent-accessible surface map was generated (FIG. 9B), again displaying the residues corresponding to peptides A in blue, peptide B in red, and peptide C in green. Functional studies indicated Val$^{334}$ and Val$^{336}$ of peptide A are required for inhibition of IL-16. The structural modeling indicated that all of these residues are solvent-accessible and therefore contribute to binding interactions with IL-16.

EXAMPLE 7

Mutagenesis experiments conducted on membrane expressed human CD4 revealed two amino acids (Leucine 348 and Leucine 349) which were required for inhibition of IL-16-induced biological activity. Point mutations at Leu 348 and Leu 349 in human CD4 were prepared as follows.

The oligonucleotide primers (Life Technologies-Gibco-BRL, Grand Island, N.Y.) used to generate human CD4 mutants were as follows:

I. glutamine 346 to asparagine 5'primer: and 3'primer:

5'-ggggggatgtggaattgtctgctgagtgac-3' (SEQ ID NO:23)

5'-gtcactcagcagacaattccacatccccgc-3' (SEQ ID NO:24)

II. leucine 348 to isole ucine 5' primer: and 3' primer:

5'-atgtggcagtgtatactgagtgactcggga-3' (SEQ ID NO:25)

5'-tcccgagtcactcagtatacactgccacat-3' (SEQ ID NO:26)

III. leucine 348 to serine 5' primer: and 3' primer:

5'-atgtggcagtgttcgctgagtgactcggga-3' (SEQ ID NO:27)

5'-tcccgagtcactcagagcacactgccacat-3' (SEQ ID NO:28)

IV. leucine 349 to isoleucine 5'primer: and 3'primer:

5'-atgtggcagtgtctgataagtgactcggga-3' (SEQ ID NO:29)

5'-tcccgactgacttatcagacactgccacat-3' (SEQ ID NO:30)

V. leucine 349 to serine 5' primer: and 3' primer:

5'-atgtggcagtgtctgtcgagtgactcggga-3' (SEQ ID NO:31)

5'-tcccgagtcactagccagacactgccacat-3' (SEQ ID NO:32)

Mutagenesis was performed using the QuikChange™ site-directed mutagenesis kit (Stratagene, LaJolla, Calif.). Initially 100 ng of wild type human CD4 CDNA (Richard Axel, Columbia University, N.Y.) contained within the mammalian expression vector pcDNA3.1 (–) (Invitrogen, Carlsbad, Calif.) was subjected to the polymerase chain reaction (PCR) in the presence of 125 ng of each set of primer pairs. PCR conditions were as follows:

| Segment | Cycles | Temp. | Time | Condition |
|---------|--------|-------|------|-----------|
| 1 | 1 | 95° C. | 30 seconds | Denaturation |
| 2 | 18 | 95° C. | 30 seconds | Denaturation |
|   |   | 55° C. | 1 minute | Annealing |
|   |   | 68° C. | 17 minutes | Elongation |

The time for the elongation step varied according to the relationship of 2 minutes per kilobase of plasmid DNA length. The product was then subjected to restriction digestion with the enzyme Dpn for 1 h. at 37° C. Dpn is specific for methylated nucleotides and therefore will only cut the original wide type CD4-plasmid DNA. The transformation reaction required the addition of 1 μl of the digest to 50 μl of Epicurean Blue *Eschericia coli* which was incubated on ice for 30 min. and finally heat shocked 42° C., 45 sec to seal the supercompent bacteria. The resultant bacteria culture was selected on ampicillin plates and sequenced to confirm mutagenesis.

Cell migration was assessed using a modified Boyden chamber. (Center, et al., (1982) *J. Immunol.* 128:2563–2568; Cruikshank, et al., (1982) *J. Immunol.* 128:2569–2574). Murine T-lymphocytes (5×10$^6$ cells/ml) in M199-HPS were loaded into the top wells of a microchemotaxis chamber, with 10$^{-9}$ M murine rIL-16 in M199-HPS (or M199-HPS alone) was added to the bottom wells. For blocking experiments, 10$^{-9}$ M murine rIL-16 with various concentrations of oligopeptides were mixed and placed in the lower well. The upper and lower wells were separated by 8 μm pore size nitrocellulose filter membrane (Neuro Probe). Following incubation (3 h, 37° C.), the membranes were removed, stained with hematoxylin, and dehydrated. Cell migration was quantified by counting the number of cells migrating beyond a depth of 40 μm. Counts were compared with control cells exposed to M199-HPS alone, which was normalized to 100%. Cell migration is expressed as the mean % control migration. All samples were tested in duplicate, with five high power fields counted in each duplicate.

Results from multiple experiments were analyzed using Student's t test for paired variables, and Tukey's test for multiple variables. A P value<0.05 was considered significant.

Figure 10A:
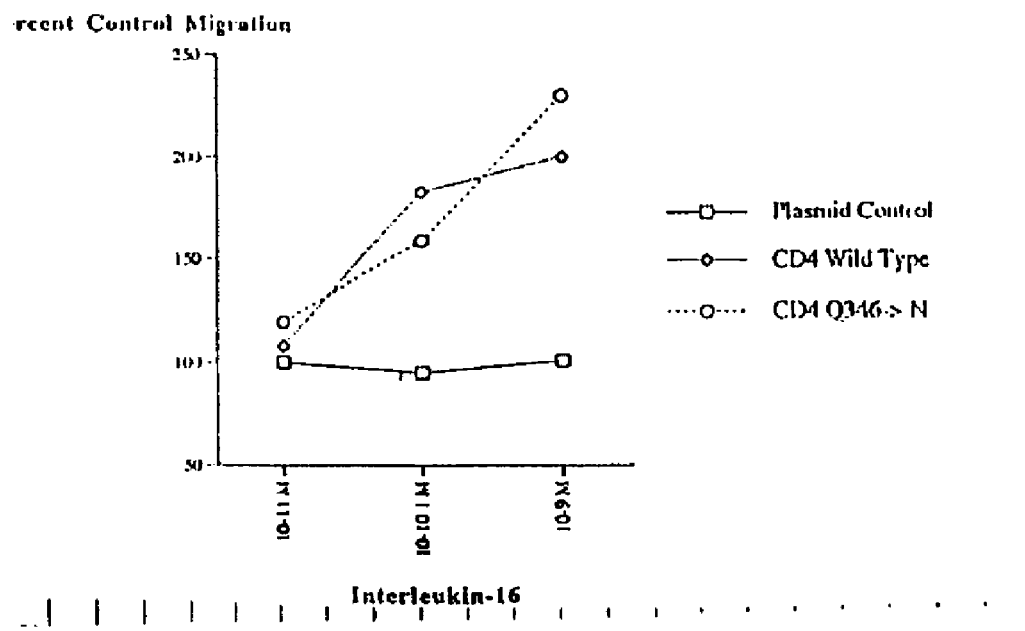
FIG. 10A Demonstrates point mutated human CD4 (Q346->N) shows no loss in inhibition of IL-16-stimulated T-lymphocytes.
Figure 10B:
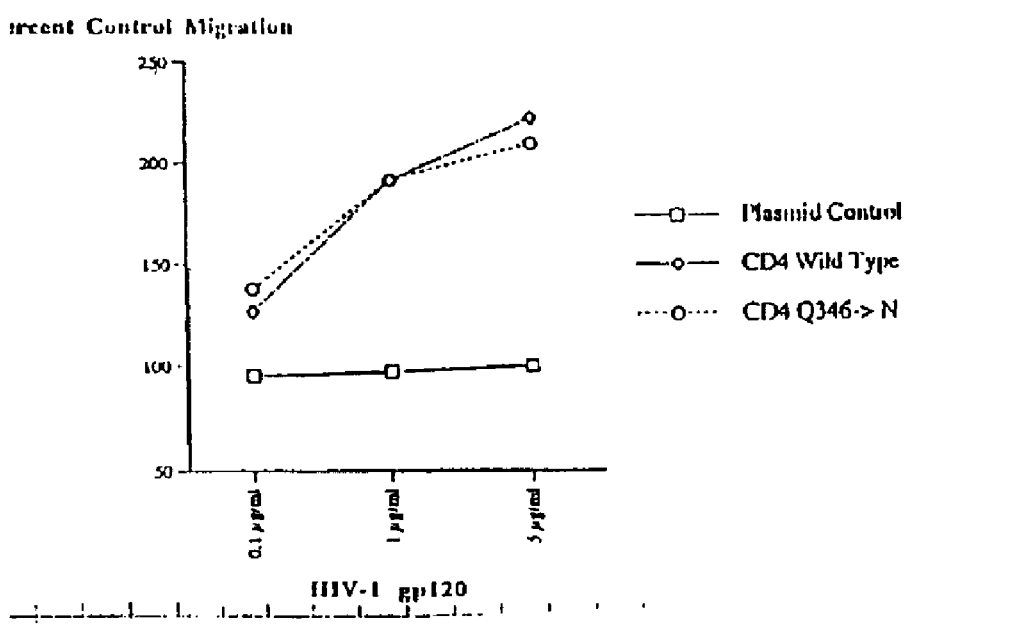
FIG. 10B Demonstrates point mutated human CD4 (Q346->N) shows no loss in inhibition of HIV-1 gp120-stimulated T-lymphocytes.
Figure 11A:
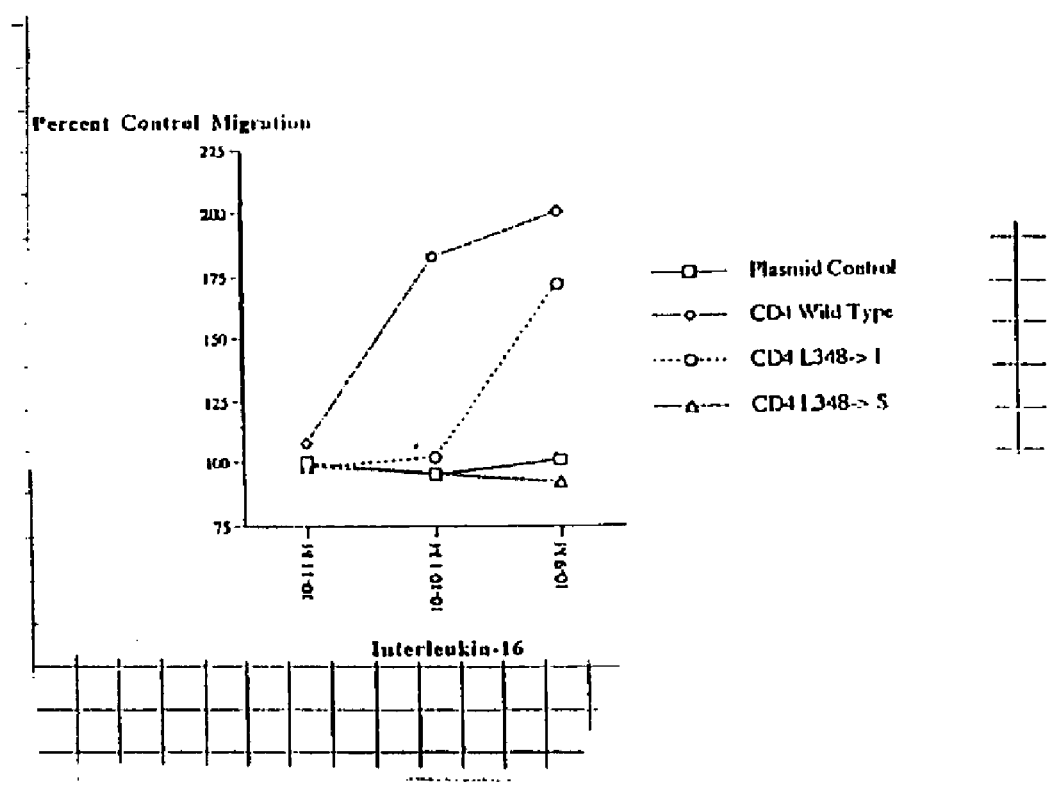
FIG. 11A Demonstrates point mutated human CD4 (L348->S) shows complete loss in inhibition of IL-16-stimulated T-lymphocytes. Partial inhibition of IL-16-stimulated T-lymphocytes was maintained where Leucine 348 was conservatively substituted with Isoleucine.
Figure 11B:
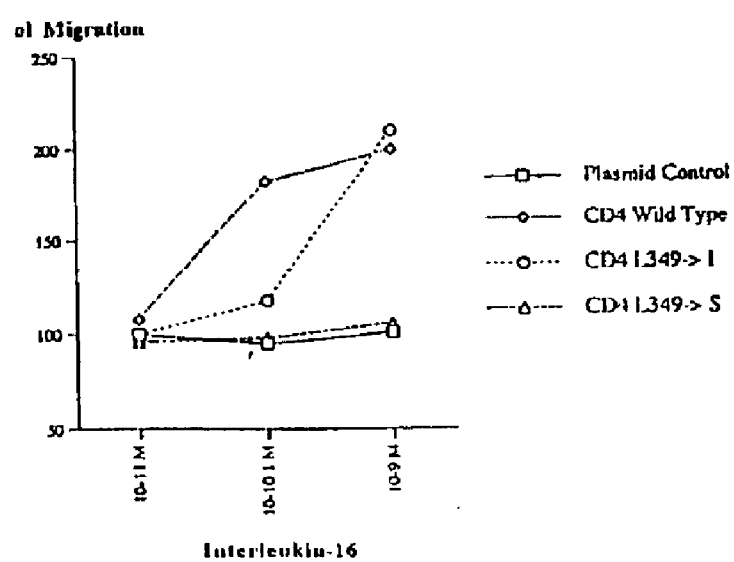
FIG. 11B Demonstrates point mutated human CD4 (L349->S) shows complete loss in inhibition of IL-16-stimulated T-lymphocytes. Partial inhibition of IL-16-stimulated T-lymphocytes was maintained where Leucine 349 was conservatively substituted with Isoleucine.

Synthetic oligopeptides based on human CD4 D4 domain sequences were prepared and tested for their ability to block murine rIL-16-stimulated and HIV-1 gp120 T-lymphocyte migration. Human CD4 D4 NLTCEVWGPTSP-KLMLSLKLENKEAKVSKREKAVWVLN-PEAGMWQCLLSDSGQVLLE SNIKVLPTWSTPVQPM, (SEQ ID NO:16) and NLTCEVWGPTSPKLMLSLKLEN-KEAKVSKREKAVWVLNPEAGMWNCLLSDSGQVLLE SNIKVLPTWSTPVQPM (CD4 Q346->N; SEQ ID NO:33), had IL-16-inhibitory activity. (FIGS. 10A and 10B). In contrast, human CD4 D4 NLTCEVWGPTSP-KLMLSLKLENKEAKVSKREKAVWVLN-PEAGMWQCSLSDSGQVLLE SNIKVLPTWSTPVQPM (CD4 L348->S; SEQ ID NO:34) and NLTCEVWGPTSP-KLMLSLKLENKEAKVSKREKAVWVLN-PEAGMWQCLSSDSGQVLLE SNIKVLPTWSTPVQPM (CD4 L349->S; SEQ ID NO:35) lost the ability to inhibit IL-16-mediated biological activity. Two additional CD4 oligopeptides with Isoleucine (conservative substitution) substituted at positions 348 (SEQ ID NO:36) and 349 (SEQ ID NO:37) maintained partial ability to inhibit IL-16-mediated biological activity. (FIGS. 11A and 11B). This assay confirmed that a non-conservative point mutation at positions 348 or 349 (e.g. L->S) destroys the ability of CD4 to inhibit IL-16-mediated biological activity (i.e. chemotaxis).

EXAMPLE 8

Figure 12:
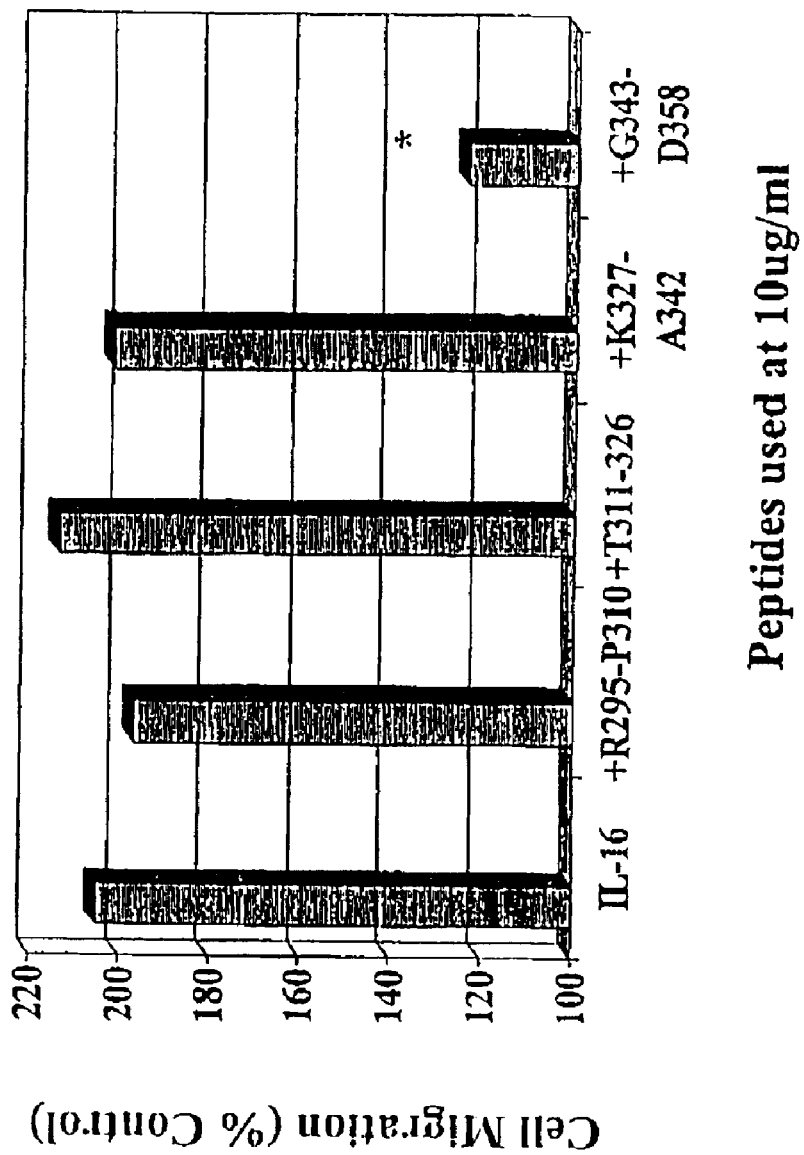
FIG. 12 Shows the effect of D4 peptides on IL-16-induced migration of human T-cells.

To confirm that the D4 domain was essential for an IL-16/CD4 interaction, peptides based on the amino acid sequence of the human CD4 D4 domain were generated. A 16 amino acid sequence encompassing the proximal portion of the D4 domain (GMWQCLLSDSGQVLLE, SEQ ID NO:12) blocked all IL-16-induced migration of human T-cells at a concentration of $10^{-10}$ M in the assay described in Example 1. In contrast, 16-mer peptides TSP-KLMLSLKLENKEA (SEQ ID NO:38) and KVSKREKAVWVLNPEA (SEQ ID NO:39) failed to effect IL-16-induced migration at any concentration. A dose curve of the peptide indicated that maximal inhibition was achieved at a concentration of 10 μg/ml and greater. (FIG. 12).

Figure 13:
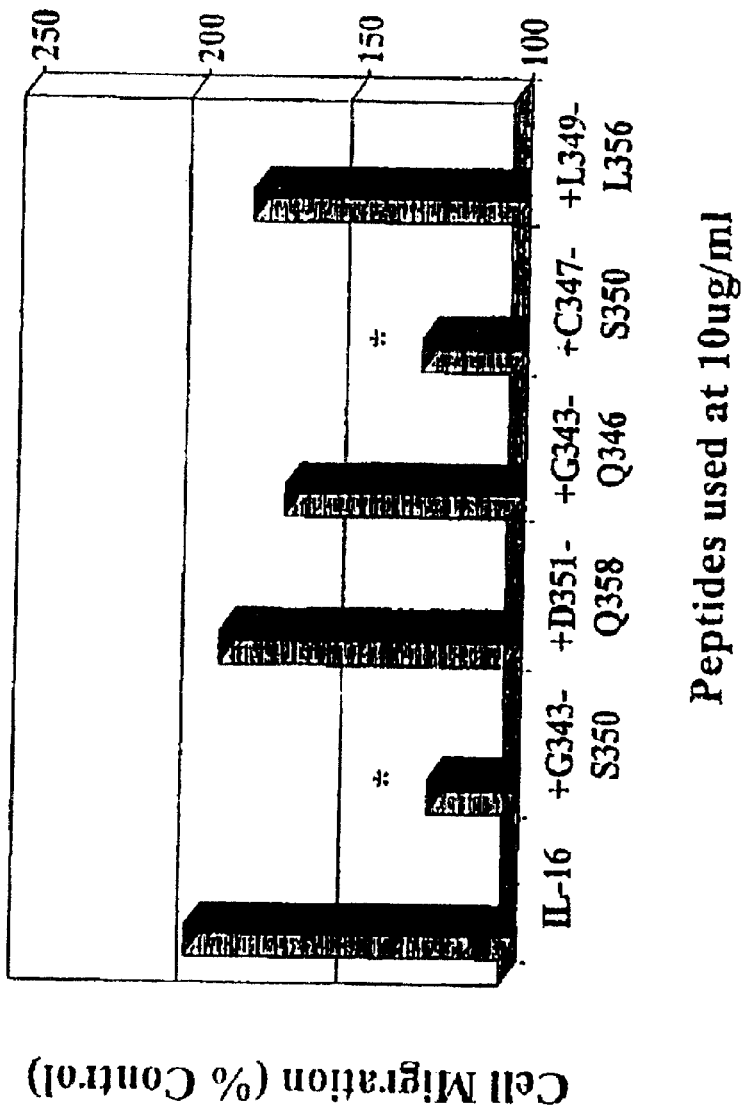
FIG. 13 Shows the effect of CD4 peptides on IL-16 Induced Migration of Human T-cells.
Figure 14:
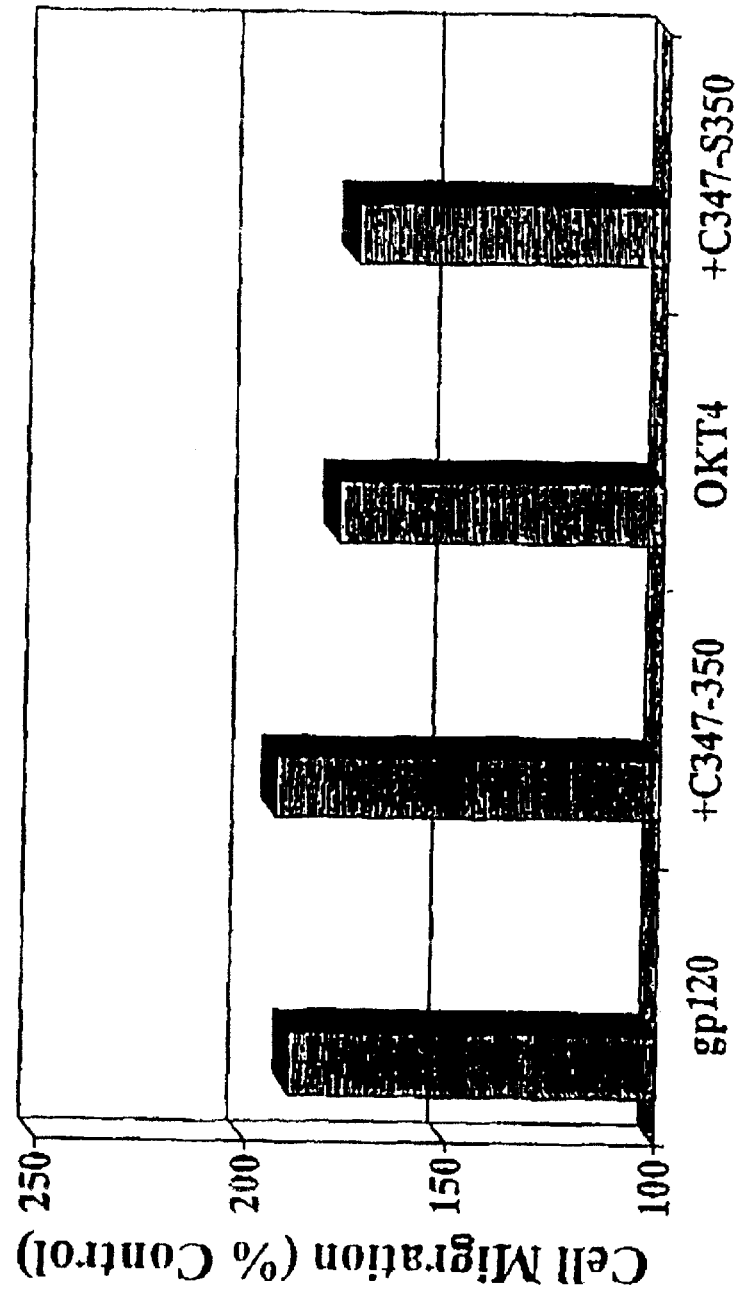
FIG. 14 Shows the effect of peptide $C^{347}$–$S^{350}$ on gp120 and OKT4 induced migration of T-cells.

To further identify the core active sequence within human CD4, two 8-residue peptides were generated. DSGQVLLE (amino acids 351:358; (SEQ ID NO:40) failed to inhibit IL-16-mediated biological activity. However, peptide GMWQCLLS (amino acids 343–350 (SEQ ID NO:13) inhibited all IL-16-mediated biological activity. The active site was further delineated by the use of tetrapeptides GMWQ (SEQ ID NO:41) and CLLS (SEQ ID NO:2). As shown in FIG. 13 co-incubation of IL-16 and CLLS blocked approximately 90% of IL-16-induced migration of human T-cells. The inhibitory activity of CLLS on IL-16 bioactivity was not as a result of disruption of normal CD4 activity, as co-incubation with two other CD4 ligands capable of inducing migration, HIV-1 gp120 (5 μg/ml) and anti-CD4 antibody (OKT4, 1 μg/ml), were unaffected. Gp120 binds to CD4 in the D1D2 region while the OKT4 antibody has been mapped to associate with CD4 in the D3 region. (FIG. 14).

These results confirm that the bioactive site for IL-16 on CD4 is located within the tetrapeptide region defined by CLLS. These results further confirm that inhibition of IL-16 induced migration by CLLS was not as a result of disruption of CD4 aggregation nor alteration of normal CD4 responsiveness to other CD4 ligands.

What is claimed is:

1. An antibody directed against an isolated IL-16 antagonist peptide consisting of CLLS (SEQ ID NO:2).

2. An antibody directed against an isolated IL-16 antagonist peptide consisting of any one of WQCLLS (SEQ ID NO:4), WQALLS (SEQ ID NO:5), VVQVVA (SEQ ID NO:9) or VKQVVA (SEQ ID NO:11).

3. An antibody directed against an isolated IL-16 antagonist peptide consisting of GMWQCLLS (SEQ ID NO:13).

4. An antibody directed against an isolated IL-16 antagonist peptide consisting of TGLWQCLLSEGD (SEQ ID NO:14).

5. An antibody directed against an isolated IL-16 antagonist peptide consisting of VSEEQKVVQVVA (SEQ ID NO:15).

6. A pharmaceutical composition comprising the antibody of any one of claim 1 3 4 or 5.

* * * * *